United States Patent
Hosse et al.

(10) Patent No.: US 9,650,442 B2
(45) Date of Patent: May 16, 2017

(54) BISPECIFIC ANTI-EGFR/ANTI IGF-1R ANTIBODIES

(71) Applicant: Roche Glycart AG, Schlieren (CH)

(72) Inventors: Ralf Hosse, Cham (CH); Christian Klein, Bonstetten (CH); Ekkehard Moessner, Kreuzlingen (CH); Juergen Michael Schanzer, Munich (DE); Cuiying Shao, Aberdeen (GB); Lei Shi, Shanghai (CN); Pablo Umana, Wollerau (CH); Peng Wang, Shanghai (CN); Katharina Wartha, Munich (DE)

(73) Assignee: Roche Glycart AG, Schilieren (CH)

( * ) Notice: Subject to any disclaimer, the term of this patent is extended or adjusted under 35 U.S.C. 154(b) by 0 days.

(21) Appl. No.: 14/220,952

(22) Filed: Mar. 20, 2014

(65) Prior Publication Data

US 2014/0193415 A1    Jul. 10, 2014

Related U.S. Application Data

(63) Continuation of application No. PCT/EP2012/068133, filed on Sep. 14, 2012.

(30) Foreign Application Priority Data

Sep. 23, 2011   (WO) ................ PCT/CN2011/080135

(51) Int. Cl.
    *C07K 16/28* (2006.01)
(52) U.S. Cl.
    CPC ...... *C07K 16/2863* (2013.01); *C07K 2317/21* (2013.01); *C07K 2317/31* (2013.01); *C07K 2317/41* (2013.01); *C07K 2317/55* (2013.01); *C07K 2317/565* (2013.01); *C07K 2317/73* (2013.01); *C07K 2317/732* (2013.01); *C07K 2317/76* (2013.01); *C07K 2317/92* (2013.01); *C07K 2319/21* (2013.01); *C07K 2319/41* (2013.01); *C07K 2319/43* (2013.01)

(58) Field of Classification Search
    None
    See application file for complete search history.

(56) References Cited

U.S. PATENT DOCUMENTS

2010/0081796 A1    4/2010   Brinkmann et al.

FOREIGN PATENT DOCUMENTS

| KR | 10-2011-0047255 | 5/2011 |
| WO | 2006/082515 A2 | 8/2006 |
| WO | 2007/062037 A2 | 5/2007 |
| WO | 2007/062037 A3 | 5/2007 |
| WO | 2009/080253 A1 | 7/2009 |
| WO | 2010/034441 | 4/2010 |

OTHER PUBLICATIONS

Paul, W.E. Fundamental Immunology, 3rd Edition, 1993, pp. 292-295.*
MacCallum R.M. et al, Antibody-antigen interactions: Contact analysis and binding site topography. J. Mol. Biol., 1998, vol. 262, p. 732-745.*
Casset F, et al. A peptide mimetic of an anti-CD4 monoclonal antibody by rational design. Biochemical and Biophysical Research Communications, 2003, vol. 307, p. 198-205.*
Bendig, M.M. Humanization of rodent monoclonal antibodies by CDR grafting. Methods: A Companion to Methods in Enzymology, 1995; vol. 8, p. 83-93.*
Dong, J. et al., "A stable IgG-like bispecific antibody targeting the epidermal growth factor receptor . . . " mAbs 3(3):273-288 ( 2011).
International Preliminary Report on Patentability for International Patent Application No. PCT/EP2012/068133.
Notification of Transmittal of ISR and Written Opinion of PCT/EP2012/068133.
Colman, "Effects of Amino Acid Sequence Changes on Antibody-Antigen Interactions" Research in Immunology 145:33-36 ( 1994).

* cited by examiner

*Primary Examiner* — Michael Pak

(57) ABSTRACT

The present invention relates to bispecific anti-EGFR/anti IGF-1R antibodies, methods for their production, pharmaceutical compositions containing said antibodies, and uses thereof.

6 Claims, 2 Drawing Sheets

BISPECIFIC ANTI-EGFR/ANTI IGF-1R ANTIBODIES

The present invention relates to bispecific anti-EGFR/anti IGF-1R antibodies, methods for their production, pharmaceutical compositions containing said antibodies, and uses thereof.

BACKGROUND OF THE INVENTION

Lu, D., et al., Biochemical and Biophysical Research Communications 318 (2004) 507-513; J. Biol. Chem., 279 (2004) 2856-2865; and J. Biol. Chem. 280 (2005) 19665-19672 relates to bispecific antibodies against human EGFR and human IGF-1R WO 2010/034441 relates to bispecific antibodies against human EGFR and human IGF-1R based on the sequences of on <IGF-1R> HUMAB Clone and humanized <EGFR>ICR62 (SEQ ID NOs: 1-16 (as listed below)).

SUMMARY OF THE INVENTION

One aspect of the invention is a bispecific antibody that binds to human EGFR and human IGF-1R comprising a first antigen-binding site that binds to human EGFR and a second antigen-binding site that binds to human IGF-1R,
i) the first antigen-binding site comprises in the heavy chain variable domain a CDR1 of SEQ ID NO:1, a CDR2 of SEQ ID NO:2, and a CDR3 of SEQ ID NO:3, and in the light chain variable domain a CDR1 of SEQ ID NO:4, a CDR2 of SEQ ID NO:5, and a CDR3 of SEQ ID NO:6; and
ii) the second antigen-binding site is a modified antigen-binding site based on the heavy chain variable domain comprising a CDR1 of SEQ ID NO:9, a CDR2 of SEQ ID NO:10, and a CDR3 of SEQ ID NO:11; and on the light chain variable domain comprising a CDR1 of SEQ ID NO: 12, a CDR2 of SEQ ID NO:13, and a CDR3 of SEQ ID NO:14;
wherein the modified second antigen-binding site comprises one more modifications in one or more of the CDRs; and
wherein the modified second antigen binding site has an at least 10-fold increased KD value of the binding affinity for binding to human IGF-1R compared to the unmodified second antigen binding site.

One embodiment of the invention is a bispecific antibody that binds to human EGFR and human IGF-1R comprising a first antigen-binding site that binds to human EGFR and a second antigen-binding site that binds to human IGF-1R, characterized in that
i) the first antigen-binding site comprises in the heavy chain variable domain a CDR1 of SEQ ID NO: 1, a CDR2 of SEQ ID NO: 2, and a CDR3 of SEQ ID NO: 3, and in the light chain variable domain a CDR1 of SEQ ID NO: 4, a CDR2 of SEQ ID NO: 5, and a CDR3 of SEQ ID NO: 6; and
ii) a) the second antigen-binding site comprises in the heavy chain variable domain a CDR1 of SEQ ID NO: 17, a CDR2 of SEQ ID NO: 18, and a CDR3 of SEQ ID NO: 19, and in the light chain variable domain a CDR1 of SEQ ID NO: 20, a CDR2 of SEQ ID NO: 21, and a CDR3 of SEQ ID NO: 22;
b) the second antigen-binding site comprises in the heavy chain variable domain a CDR1 of SEQ ID NO: 25, a CDR2 of SEQ ID NO: 26, and a CDR3 of SEQ ID NO: 27, and in the light chain variable domain a CDR1 of SEQ ID NO: 28, a CDR2 of SEQ ID NO: 29, and a CDR3 of SEQ ID NO: 30;
c) the second antigen-binding site comprises in the heavy chain variable domain a CDR1 of SEQ ID NO: 33, a CDR2 of SEQ ID NO: 34, and a CDR3 of SEQ ID NO: 35, and in the light chain variable domain a CDR1 of SEQ ID NO: 36, a CDR2 of SEQ ID NO: 37, and a CDR3 of SEQ ID NO: 38;
d) the second antigen-binding site comprises in the heavy chain variable domain a CDR1 of SEQ ID NO: 41, a CDR2 of SEQ ID NO: 42, and a CDR3 of SEQ ID NO: 43, and in the light chain variable domain a CDR1 of SEQ ID NO: 44, a CDR2 of SEQ ID NO: 45, and a CDR3 of SEQ ID NO: 46; or
e) the second antigen-binding site comprises in the heavy chain variable domain a CDR1 of SEQ ID NO: 49, a CDR2 of SEQ ID NO: 50, and a CDR3 of SEQ ID NO: 51, and in the light chain variable domain a CDR1 of SEQ ID NO: 52, a CDR2 of SEQ ID NO: 53, and a CDR3 of SEQ ID NO: 54.

One embodiment of the invention is a bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8;
ii) a) the second antigen-binding site comprises a heavy chain variable domain VH of SEQ ID NO: 23, and a light chain variable domain VL of SEQ ID NO: 24;
b) the second antigen-binding site comprises a heavy chain variable domain VH of SEQ ID NO: 31, and a light chain variable domain VL of SEQ ID NO: 32;
c) the second antigen-binding site comprises a heavy chain variable domain VH of SEQ ID NO: 39, and a light chain variable domain VL of SEQ ID NO: 40;
d) the second antigen-binding site comprises a heavy chain variable domain VH of SEQ ID NO: 47, and a light chain variable domain VL of SEQ ID NO: 48; or
e) the second antigen-binding site comprises a heavy chain variable domain VH of SEQ ID NO: 55, and a light chain variable domain VL of SEQ ID NO: 56.

In one embodiment the bispecific antibody according to the invention is characterized in that said antibody is bivalent, trivalent or tetravalent.

In one embodiment the bispecific antibody according to the invention is characterized in that said antibody is glycosylated with a sugar chain at Asn297 whereby the amount of fucose within said sugar chain is 65% or lower.

One embodiment of the invention is a pharmaceutical formulation comprising a bispecific antibody according to the invention.

One embodiment of the invention is a bispecific antibody according to the invention for use in the treatment of cancer.

One embodiment of the invention is the use of a bispecific antibody according to the invention for the manufacture of a medicament for the treatment of cancer.

One embodiment of the invention is a method of treatment of patient suffering from cancer by administering a bispecific antibody according to the invention to a patient in the need of such treatment.

One embodiment of the invention is a nucleic acid encoding a bispecific antibody according to the invention. One embodiment of the invention are expression vectors characterized by comprising said nucleic acid for the expression of a bispecific antibody according to the invention in a host cell. One embodiment of the invention is a host cell comprising said expression vector. One embodiment of the invention is a method for the production of a bispecific antibody according to the invention, characterized by expressing said nucleic acid in a host cell and recovering said bispecific antibody from said cell or the cell culture supernatant.

Such bispecific anti-EGFR/anti-IGF-1R antibodies have highly valuable properties like highly effective tumor cell viability inhibition and tumor growth inhibition, inhibition both IGF-1R and IGF-1R signaling (e.g. phosphorylation). They have valuable binding properties like high binding affinity and also efficient cellular binding. They show high ADCC activity especially when they are glycoengineered. The bispecific anti-EGFR/anti-IGF-1R antibodies according to the invention furthermore have are highly stable under stress, which is important for production and their pharmacokinectic properties.

DETAILED DESCRIPTION OF THE INVENTION

Figure 1A:
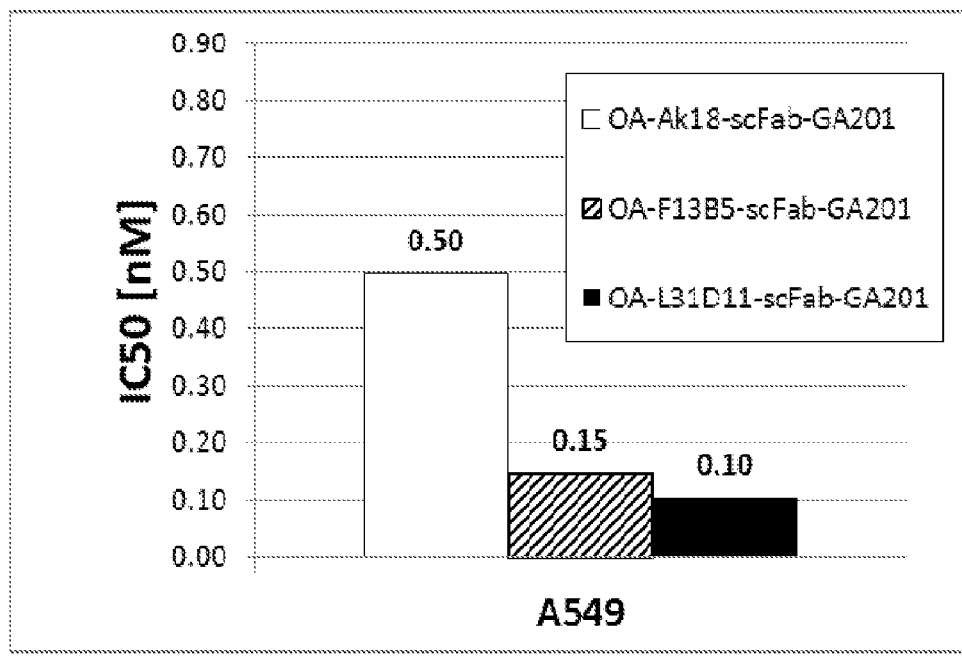
FIGS. 1a and 1b Inhibition of cancer cell proliferation of A549 cancer cells (FIG. 1a) and of RD-ES cancer cells (FIG. 1b) by the modified bispecific <EGFR-IGF1R> antibodies OA-F13B5-scFab-GA201 and OA-L31D11-scFab-GA201 in comparison with <EGFR-IGF1R> antibody OA-Ak18-scFab-GA201. The potency is markedly increased for the affinity maturated bispecific antibodies according to the invention OA-F13B5-scFab-GA201 and OA-L31D11-scFab-GA201.

As used herein, "antibody" refers to a binding protein that comprises antigen-binding sites. The terms "binding site" or "antigen-binding site" as used herein denotes the region(s) of an antibody molecule to which a ligand actually binds. The binding sites in a bispecific antibody according to the invention may be each formed by a pair of two variable domains, i.e. of one heavy chain variable domain and one light chain variable domain. The minimal binding site determinant in an antibody is the heavy chain CDR3. In one embodiment of the current invention each of the binding sites comprises an antibody heavy chain variable domain (VH) and/or an antibody light chain variable domain (VL), and preferably is formed by a pair consisting of an antibody light chain variable domain (VL) and an antibody heavy chain variable domain (VH).

"Antibody specificity" refers to selective recognition of the antibody for a particular epitope of an antigen. Natural antibodies, for example, are monospecific. "Bispecific antibodies" according to the invention are antibodies which have two different antigen-binding specificities. Where an antibody has more than one specificity, the recognized epitopes may be associated with a single antigen or with more than one antigen. Antibodies of the present invention are specific for two different antigens, i.e. EGFR as first antigen and IGF-1R as second antigen.

The term "monospecific" antibody as used herein denotes an antibody that has one or more binding sites each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding site, four binding sites, and six binding sites, respectively, in an antibody molecule. The bispecific antibodies according to the invention are at least "bivalent" and may be "trivalent" or "multivalent" (e.g. ("tetravalent" or "hexavalent"). Preferably the bispecific antibody according to the invention is bivalent, trivalent or tetravalent. In one embodiment said bispecific antibody is bivalent. In one embodiment said bispecific antibody is trivalent. In one embodiment said bispecific antibody is tetravalent Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for a human EGFR, a second binding site is specific for human IGF-1R.

Like natural antibodies, an antigen binding site of an antibody of the invention typically contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

In certain embodiments, antibodies of the invention further comprise immunoglobulin constant regions of one or more immunoglobulin classes. Immunoglobulin classes include IgG, IgM, IgA, IgD, and IgE isotypes and, in the case of IgG and IgA, their subtypes. In one embodiment, an antibody of the invention has a constant domain structure of an IgG type antibody The terms "monoclonal antibody" or "monoclonal antibody composition" as used herein refer to a preparation of antibody molecules of a single amino acid composition.

The term "chimeric antibody" refers to an antibody comprising a variable domain, i.e., binding region, from one source or species and at least a portion of a constant region derived from a different source or species, usually prepared by recombinant DNA techniques. Chimeric antibodies comprising a murine variable domain and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable domains and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G. J. Mol. Biol. 227 (1992) 381-388; Marks, J. D., et al., J. Mol. Biol. 222 (1991) 581-597). The techniques of Cole, et al. and Boerner, et al. are also available for the preparation of human monoclonal antibodies (Cole, S. P. C., et al., Monoclonal Antibodies and Cancer Therapy, Alan R. Liss (1985) 77-96; and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four framework (FR) regions whose sequences are widely conserved, connected by three "hypervariable regions" (or complementarity determining regions, CDRs). The framework regions adopt a beta-sheet conformation and the CDRs may form loops connecting the beta-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention. (See, e.g., Kindt, T. J., et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano, S., et al., J. Immunol. 150 (1993) 880-887; Clackson, T., et al., Nature 352 (1991) 624-628).

The terms "complementarity determining regions" or "hypervariable region" when used herein refer to the amino acid residues of an antibody which are responsible for antigen-binding. The hypervariable region comprises amino acid residues from the "complementarity determining regions" or "CDRs". "Framework" or "FR" regions are those variable domain regions other than the "complementarity determining regions" residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991) NIH Publication No. 91-3242.

The bispecific antibodies according to the invention include, in addition to the affinity maturation of the CDRs of the <IGF-1R> antigen binding site which results in increased <IGF-1R> binding affinity, antibodies having "conservative sequence modifications". This means nucleotide and amino acid sequence modifications which do not affect or alter the herein-mentioned characteristics of the bispecific antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a bispecific <EGFR-IGF1R> antibody can be preferably replaced with another amino acid residue from the same side chain family. Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033.

As used herein, the terms "binding to", "specifically binding to", "that binds to" or that specifically binds to" are used interchangeably and refer to the binding of the antibody to an epitope of an antigen in an in vitro assay, preferably in a surface plasmon resonance (SPR) assay. "Binding to", "specifically binding to", "that binds to" or that specifically binds to" means that the antibody/antigen-binding site binds to the respective antigen with a KD value of the binding affinity (KD) of $1.0 \times 10^{-8}$ M or less, in one embodiment with a KD of $5.0 \times 10^{-9}$ M or less, in one embodiment with a KD between $2.0 \times 10^{-9}$ M and $1.0 \times 10^{-13}$ M. The affinity of the binding is defined by the terms ka (rate constant for the association of the antibody from the antibody/antigen complex), kd (dissociation constant), and KD (kd/ka). The binding affinity is determined with a surface plasmon resonance technique (e.g. BIAcore®, GE-Healthcare Uppsala, Sweden.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

Human epidermal growth factor receptor (also known as HER-1 or Erb-B1, and referred to herein as "EGFR") is a 170 kDa transmembrane receptor encoded by the c-erbB proto-oncogene, and exhibits intrinsic tyrosine kinase activity (Modjtahedi, H., et al., Br. J. Cancer 73 (1996) 228-235; Herbst, R. S., and Shin, D. M., Cancer 94 (2002) 1593-1611). SwissProt database entry P00533 provides the sequence of EGFR (SEQ ID NO: 75). There are also isoforms and variants of EGFR (e.g., alternative RNA transcripts, truncated versions, polymorphisms, etc.) including but not limited to those identified by Swissprot database entry numbers P00533-1, P00533-2, P00533-3, and P00533-4. EGFR is known to bind ligands including a), epidermal growth factor (EGF), transforming growth factor-α(TGf-amphiregulin, heparin-binding EGF (hb-EGF), betacellulin, and epiregulin (Herbst, R. S., and Shin, D. M., Cancer 94 (2002) 1593-1611; Mendelsohn, J., and Baselga, J., Oncogene 19 (2000) 6550-6565). EGFR regulates numerous cellular processes via tyrosine-kinase mediated signal transduction pathways, including, but not limited to, activation of signal transduction pathways that control cell proliferation, differentiation, cell survival, apoptosis, angiogenesis, mitogenesis, and metastasis (Atalay, G., et al., Ann. Oncology 14 (2003) 1346-1363; Tsao, A. S., and Herbst, R. S., Signal 4 (2003) 4-9; Herbst, R. S., and Shin, D. M., Cancer 94 (2002) 1593-1611; Modjtahedi, H., et al., Br. J. Cancer 73 (1996) 228-235).

Human insulin-like growth factor I receptor (human IGF-IR; synonyms IGF-1R, CD 221 antigen) belongs to the family of transmembrane protein tyrosine kinases (LeRoith, D., et al., Endocrin. Rev. 16 (1995) 143-163; and Adams, T. E., et al., Cell. Mol. Life. Sci. 57 (2000) 1050-1063). SwissProt database entry P08069 provides the sequence of IGF-1R (SEQ ID NO: 76). IGF-IR binds IGF I with high affinity and initiates the physiological response to this ligand in vivo. IGF IR also binds to IGF II, however with slightly lower affinity. IGF IR overexpression promotes the neoplastic transformation of cells and there exists evidence that IGF IR is involved in malignant transformation of cells and is therefore a useful target for the development of therapeutic agents for the treatment of cancer (Adams, T. E., et al., Cell. Mol. Life. Sci. 57 (2000) 1050-1063).

Compositions and Methods

In one aspect, the invention is based, in part, on a bispecific antibody that binds to human EGFR and human IGF-1R comprising a first antigen-binding site that binds to human EGFR and a second antigen-binding site that binds to human IGF-1R, i) the first antigen-binding site comprises in the heavy chain variable domain a CDR1 of SEQ ID NO:1, a CDR2 of SEQ ID NO:2, and a CDR3 of SEQ ID NO:3, and in the light chain variable domain a CDR1 of SEQ ID NO: 4, a CDR2 of SEQ ID NO:5, and a CDR3 of SEQ ID NO:6; and ii) the second antigen-binding site is a modified antigen-binding site based on the heavy chain variable domain comprising a CDR1 of SEQ ID NO:9, a CDR2 of SEQ ID NO:10, and a CDR3 of SEQ ID NO:11; and on the light chain variable domain comprising a CDR1 of SEQ ID NO: 12, a CDR2 of SEQ ID NO:13, and a CDR3 of SEQ ID NO:14;

wherein the modified second antigen-binding site comprises one more modifications in one or more of the CDRs; and wherein the modified second antigen binding site has an at least 10-fold increased KD value of the binding affinity for binding to human IGF-1R compared to the unmodified second antigen binding site.

The "unmodified second antigen binding site" comprises in the heavy chain variable domain a CDR1 of SEQ ID NO: 9, a CDR2 of SEQ ID NO: 10, and a CDR3 of SEQ ID NO:11, and in the light chain variable domain a CDR1 of SEQ ID NO: 12, a CDR2 of SEQ ID NO:13, and a CDR3 of SEQ ID NO:14.

These bispecific antibodies are new modified bispecific anti-EGFR/anti-IGF-1R antibodies with increased binding affinity which have been derived via affinity maturation of the <IGF-1R> antigen binding site of an anti-EGFR/anti-IGF-1R described in WO 2010/034441 which was based on <IGF-1R> HUMAB Clone 18 (SEQ ID NOs: 9-16) and humanized <EGFR>ICR62 (SEQ ID NOs: 1-8).

One embodiment of the invention is a bispecific antibody that binds to human EGFR and human IGF-1R comprising a first antigen-binding site that binds to human EGFR and a second antigen-binding site that binds to human IGF-1R, i) the first antigen-binding site comprises in the heavy chain variable domain a CDR1 of SEQ ID NO: 1, a CDR2 of SEQ ID NO: 2, and a CDR3 of SEQ ID NO:3, and in the light chain variable domain a CDR1 of SEQ ID NO: 4, a CDR2 of SEQ ID NO:5, and a CDR3 of SEQ ID NO:6; and ii) the second antigen-binding site is a modified antigen-binding site based on the heavy chain variable domain comprising a CDR1 of SEQ ID NO:9, a CDR2 of SEQ ID NO:10, and a CDR3 of SEQ ID NO:11; and on the light chain variable domain comprising a CDR1 of SEQ ID NO: 12, a CDR2 of SEQ ID NO:13, and a CDR3 of SEQ ID NO:14;

wherein the modified second antigen-binding site comprises one more modifications in one or more of the CDRs of the heavy chain variable domain and/or the light chain variable domain; and wherein the modified second antigen binding site has an at least 10-fold increased KD value of the binding affinity for binding to human IGF-1R compared to the unmodified second antigen binding site.

One embodiment of the invention is a bispecific antibody that binds to human EGFR and human IGF-1R comprising a first antigen-binding site that binds to human EGFR and a second antigen-binding site that binds to human IGF-1R,
i) the first antigen-binding site comprises in the heavy chain variable domain a CDR1 of SEQ ID NO: 1, a CDR2 of SEQ ID NO: 2, and a CDR3 of SEQ ID NO:3, and in the light chain variable domain a CDR1 of SEQ ID NO: 4, a CDR2 of SEQ ID NO:5, and a CDR3 of SEQ ID NO:6; and
ii) the second antigen-binding site is a modified antigen-binding site based on the heavy chain variable domain comprising a CDR1 of SEQ ID NO:9, a CDR2 of SEQ ID NO:10, and a CDR3 of SEQ ID NO:11; and on the light chain variable domain comprising a CDR1 of SEQ ID NO: 12, a CDR2 of SEQ ID NO:13, and a CDR3 of SEQ ID NO:14;
wherein the modified second antigen-binding site comprises one more modifications in one or more of the CDRs of the light chain variable domain; and
wherein the modified second antigen binding site has an at least 10-fold increased KD value of the binding affinity for binding to human IGF-1R compared to the unmodified second antigen binding site.

The term "one or more modifications in one or more of the CDRs" as used herein refers to one up to five (in one embodiment one up to three, in one embodiment two up to five, in embodiment two or three) modifications (in total) such as amino acid substitutions, deletions and/or insertions, wherein independently of each other each CDR comprises between 0 and 3 modifications. In one embodiment the modifications are amino acid substitutions.

The term "at least 10-fold increased KD value of the binding affinity compared to the unmodified antigen binding site" as used herein refers an increase of the KD value of the binding affinity to human IGF-1R of 10-fold or more of the modified affinity maturated <IGF-1R> antigen binding sites compared to the unmodified (=parental) antigen binding site of <IGF-1R> HUMAB Clone 18 (SEQ ID NOs: 9-16). To determine the increase of the binding affinity the KD values of the modified affinity maturated <IGF-1R> antigen binding sites and of the unmodified parental <IGF-1R> HUMAB Clone 18 (SEQ ID NOs: 9-16) are determined via their Fab fragments in a Surface Plasmon Resonance assay at 25° C. as described in detail in Example 1. The increase of the KD value is calculated as the ratio KD (unmodified)/KD (modified).

One embodiment of the invention a bispecific antibody that binds to human EGFR and human IGF-1R comprising a first antigen-binding site that binds to human EGFR and a second antigen-binding site that binds to human IGF-1R,
i) the first antigen-binding site comprises a heavy chain variable domain of SEQ ID NO:7, and a light chain variable domain of SEQ ID NO:8; and
ii) the second antigen-binding site is a modified antigen-binding site based on the heavy chain variable domain of SEQ ID NO:15; and
on the light chain variable domain of SEQ ID NO: 16;
wherein the modified second antigen-binding site comprises one more modifications in one or more of the CDRs; and
wherein the modified second antigen binding site has an at least 10-fold increased KD value of the binding affinity for binding to human IGF-1R compared to the unmodified second antigen binding site.

The "unmodified antigen binding site" comprises a heavy chain variable domain VH of SEQ ID NO: 15, and a light chain variable domain VL of SEQ ID NO: 16.

One embodiment of the invention is a bispecific antibody that binds to human EGFR and human IGF-1R comprising a first antigen-binding site that binds to human EGFR and a second antigen-binding site that binds to human IGF-1R,
i) the first antigen-binding site comprises a heavy chain variable domain of SEQ ID NO:7, and a light chain variable domain of SEQ ID NO:8; and
ii) the second antigen-binding site is a modified antigen-binding site based on the heavy chain variable domain of SEQ ID NO:15; and on the light chain variable domain of SEQ ID NO: 16;
wherein the modified second antigen-binding site comprises one more modifications in one or more of the CDRs of the heavy chain variable domain and/or the light chain variable domain; and
wherein the modified second antigen binding site has an at least 10-fold increased KD value of the binding affinity for binding to human IGF-1R compared to the unmodified second antigen binding site.

One embodiment of the invention is a bispecific antibody that binds to human EGFR and human IGF-1R comprising a first antigen-binding site that binds to human EGFR and a second antigen-binding site that binds to human IGF-1R,
i) the first antigen-binding site comprises a heavy chain variable domain of SEQ ID NO:7, and a light chain variable domain of SEQ ID NO:8; and
ii) the second antigen-binding site is a modified antigen-binding site based on the heavy chain variable domain of SEQ ID NO:15; and on the light chain variable domain of SEQ ID NO: 16;
wherein the modified second antigen-binding site comprises one more modifications in one or more of the CDRs of the light chain variable domain; and
wherein the modified second antigen binding site has an at least 10-fold increased KD value of the binding affinity for binding to human IGF-1R compared to the unmodified second antigen binding site.

Thus one embodiment of the invention is a bispecific antibody that binds to human EGFR and human IGF-1R comprising a first antigen-binding site that binds to human EGFR and a second antigen-binding site that binds to human IGF-1R, characterized in that
i) the first antigen-binding site comprises in the heavy chain variable domain a CDR1 of SEQ ID NO:1, a CDR2 of SEQ ID NO:2, and a CDR3 of SEQ ID NO:3, and in the light chain variable domain a CDR1 of SEQ ID NO:4, a CDR2 of SEQ ID NO:5, and a CDR3 of SEQ ID NO:6; and
ii) a) the second antigen-binding site comprises in the heavy chain variable domain a CDR1 of SEQ ID NO:17, a CDR2 of SEQ ID NO: 18, and a CDR3 of SEQ ID NO:19, and in the light chain variable domain a CDR1 of SEQ ID NO: 20, a CDR2 of SEQ ID NO:21, and a CDR3 of SEQ ID NO:22;
b) the second antigen-binding site comprises in the heavy chain variable domain a CDR1 of SEQ ID NO:25, a CDR2 of SEQ ID NO: 26, and a CDR3 of SEQ ID NO:27, and in the light chain variable domain a CDR1 of SEQ ID NO:28, a CDR2 of SEQ ID NO:29, and a CDR3 of SEQ ID NO:30;
c) the second antigen-binding site comprises in the heavy chain variable domain a CDR1 of SEQ ID NO:33, a CDR2 of SEQ ID NO:34, and a CDR3 of SEQ ID NO:35, and in the light chain variable domain a CDR1 of SEQ ID NO:36, a CDR2 of SEQ ID NO:37, and a CDR3 of SEQ ID NO:38;
d) the second antigen-binding site comprises in the heavy chain variable domain a CDR1 of SEQ ID NO:41, a CDR2 of SEQ ID NO:42, and a CDR3 of SEQ ID NO:43, and in the light chain variable domain a CDR1 of SEQ ID NO:44, a CDR2 of SEQ ID NO:45, and a CDR3 of SEQ ID NO:46; or
e) the second antigen-binding site comprises in the heavy chain variable domain a CDR1 of SEQ ID NO:49, a CDR2 of SEQ ID NO:50, and a CDR3 of SEQ ID NO:51, and in the light chain variable domain a CDR1 of SEQ ID NO:52, a CDR2 of SEQ ID NO:53, and a CDR3 of SEQ ID NO:54.

One embodiment of the invention is bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8; and
ii) a) the second antigen-binding site comprises a heavy chain variable domain VH of SEQ ID NO: 23, and a light chain variable domain VL of SEQ ID NO: 24;
b) the second antigen-binding site comprises a heavy chain variable domain VH of SEQ ID NO: 31, and a light chain variable domain VL of SEQ ID NO: 32;
c) the second antigen-binding site comprises a heavy chain variable domain VH of SEQ ID NO: 39, and a light chain variable domain VL of SEQ ID NO: 40;
d) the second antigen-binding site comprises a heavy chain variable domain VH of SEQ ID NO: 47, and a light chain variable domain VL of SEQ ID NO: 48; or
e) the second antigen-binding site comprises a heavy chain variable domain VH of SEQ ID NO: 55, and a light chain variable domain VL of SEQ ID NO: 56.

One embodiment of the invention is bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8; and
ii) the second antigen-binding site comprises a heavy chain variable domain VH of SEQ ID NO: 23, and a light chain variable domain VL of SEQ ID NO: 24.

One embodiment of the invention is bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8; and
ii) the second antigen-binding site comprises a heavy chain variable domain VH of SEQ ID NO: 31, and a light chain variable domain VL of SEQ ID NO: 32.

One embodiment of the invention is bispecific antibody that binds to human EGFR and human IGF-1R comprising a first antigen-binding site that binds to EGFR and a second antigen-binding site that binds to IGF-1R, characterized in that
i) the first antigen-binding site comprises a heavy chain variable domain VH of SEQ ID NO: 7, and a light chain variable domain VL of SEQ ID NO: 8; and
ii) the second antigen-binding site comprises a heavy chain variable domain VH of SEQ ID NO: 39, and a light chain variable domain VL of SEQ ID NO: 40.

One embodiment of the invention is bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8; and
ii) the second antigen-binding site comprises a heavy chain variable domain VH of SEQ ID NO: 47, and a light chain variable domain VL of SEQ ID NO: 48.

One embodiment of the invention is bispecific antibody that binds to human EGFR and human IGF-1R comprising a first antigen-binding site that binds to human EGFR and a second antigen-binding site that binds to human IGF-1R, characterized in that
i) the first antigen-binding site comprises a heavy chain variable domain VH of SEQ ID NO: 7, and a light chain variable domain VL of SEQ ID NO: 8; and
ii) the second antigen-binding site comprises a heavy chain variable domain VH of SEQ ID NO: 55, and a light chain variable domain VL of SEQ ID NO: 56.

Such bispecific anti-EGFR/anti-IGF-1R antibodies have highly valuable properties like highly effective tumor cell viability inhibition and tumor growth inhibition, inhibition both IGF-1R and IGF-1R signaling (e.g. phosphorylation). They have valuable binding properties like high binding affinity and also efficient cellular binding. They show high ADCC activity especially when they are glycoengineered (GE).

In one embodiment of the invention the bispecific antibodies according to the invention inhibit the IGF-1R phosphorylation and EGFR phosphorylation (see Example 4). In one embodiment the bispecific antibodies according to the invention inhibit IGF-1R phosphorylation in A549 cancer cells with an IC50 of 0.10 nM or lower. In one embodiment the bispecific antibodies according to the invention inhibit IGF-1R phosphorylation in BxPC3 cancer cells with an IC50 of 0.10 nM or lower. In one embodiment the bispecific antibodies according to the invention inhibit IGF-1R phosphorylation in TC-71 cancer cells with an IC50 of 0.10 nM or lower. In one embodiment the bispecific antibodies according to the invention inhibit EGFR phosphorylation in A549 cancer cells with an IC50 of 0.23 nM or lower. In one embodiment the bispecific antibodies according to the invention inhibit EGFR phosphorylation in BxPC3 cancer cells with an IC50 of 0.90 nM or lower.

In one embodiment of the invention the bispecific antibodies according to the invention inhibit the cancer cell proliferation or tumor cell proliferation (see Example 5). In one embodiment the bispecific antibodies according to the invention inhibit proliferation of A549 cancer cells with an IC50 of 0.20 nM or lower (preferably with an IC50 of 0.15 nM or lower). In one embodiment the bispecific antibodies according to the invention inhibit proliferation of RD-ES cancer cells with an IC50 of 0.10 nM or lower (preferably with an IC50 of 0.05 nM or lower).

In one embodiment of the invention the bispecific antibodies according to the invention are glycoengineered with an amount of fucose of 65% or lower (preferably between 50 and 5%) and induce ADCC in cancer cells (see Example 7).

In one embodiment of the invention the bispecific antibodies according to the invention are glycoengineered with an amount of fucose of 65% or lower (preferably between 50 and 5%) and induce ADCC in H460M2 cancer cells with an EC50 of 0.10 nM or lower. In one embodiment of the invention the bispecific antibodies according to the invention are glycoengineered with an amount of fucose of 65% or lower (preferably between 50 and 5%) and induce ADCC in H322M cancer cells with an EC50 of 0.15 nM or lower. Thus the bispecific antibodies of the invention are useful, e.g., for the diagnosis or treatment of cancer In one embodiment said bispecific antibody is bivalent—using formats as described e.g. a) in WO 2009/080251, WO 2009/080252, WO 2009/080253 or Schaefer et al, PNAS 108 (2011) 11187-11192 (domain exchanged antibodies—see Example 2—CrossMabs (CM) of SEQ ID NOs: 63-66 or of SEQ ID NOs: 67-70) or e.g. b) in EP Appl. No 10003270.5 (—see Example 2 see OA-scFabs of SEQ ID NOs: 57-59) or of SEQ ID NOs: 60-62)) or e.g. c) in Ridgway, J. B., Protein Eng. 9 (1996) 617-621; WO 96/027011; Merchant, A. M, et al., Nature Biotech 16 (1998) 677-681; Atwell, S., et al., J. Mol. Biol. 270 (1997) 26-35 and EP 1 870 459 A1.

In one embodiment the bispecific antibody according to the invention is characterized in comprising as amino acid sequences of SEQ ID NO: 57, SEQ ID NO: 58, and SEQ ID NO: 59. In one embodiment the bispecific antibody according to the invention is characterized in comprising as amino acid sequences of SEQ ID NO: 60, SEQ ID NO: 61, and SEQ ID NO: 62. In one embodiment the bispecific antibody according to the invention is characterized in comprising as amino acid sequences of SEQ ID NO: 63, SEQ ID NO: 64, SEQ ID NO: 65 and SEQ ID NO: 66. In one embodiment the bispecific antibody according to the invention is characterized in comprising as amino acid sequences of SEQ ID NO: 67, SEQ ID NO: 68, SEQ ID NO: 69 and SEQ ID NO: 70 thereof. These amino acid sequences are based on the antigen-binding sites of a) <IGF-1R> F13B5 (SEQ ID NOs: 17-24) or <IGF-1R> L31D11 (SEQ ID NOs: 41-48) (both are affinity matured HUMAB <IGF-1R> Clone 18 antibodies) and b) humanized <EGFR>ICR62 (SEQ ID NOs: 1-8; see also WO 2006/082515 abbreviated as <EGFR>ICR62).

In one embodiment said bispecific antibody is trivalent using e.g. formats based on a full length antibody specifically binding to one of the two receptors EGFR or IGF-1R, to which only at one C-terminus/or N-terminus of one heavy chain a scFab fragment is fused which specifically binds to the other of the two receptors EGFR or IGF-1R, including knobs—into holes technology, as described e.g. in WO 2010/112193 or e.g. formats based on a full length antibody specifically binding to one of the two receptors EGFR or IGF-1R, to which at one C-terminus of one heavy chain a VH or VH-CH$_1$ fragment and at the other C-terminus of the second heavy chain a VL or VL-CL fragment is fused which specifically binds to the other of the two receptors EGFR or IGF-1R, including knobs into holes technology, as described e.g. in WO 2010/115589. Other trivalent formats are described e.g. in EP Application No. 10173914.2. For the knobs into holes technology and variations thereof see also Ridgway, J. B., Protein Eng. 9 (1996) 617-621; WO 96/027011, Merchant, A. M, et al., Nature Biotech 16 (1998) 677-681; Atwell, S., et al., J. Mol. Biol. 270 (1997) 26-35; and EP 1 870 459 A1.

In one embodiment said bispecific antibody is tetravalent using formats as described e.g. in WO 2007/024715, WO 2007/109254, WO 2010/112193, WO 2010/145792, or WO2010/145793 (see e.g. Examples 2 Tv-L31D11-GA201 and Tv-F13B5-GA201).

In one embodiment the bispecific antibody according to the invention is characterized in comprising as amino acid sequences of SEQ ID NO: 71, and SEQ ID NO: 72. In one embodiment the bispecific antibody according to the invention is characterized in comprising as amino acid sequences of SEQ ID NO: 73, and SEQ ID NO: 74. These amino acid sequences are based on the antigen-binding sites of a)<IGF-1R> F13B5 (SEQ ID NOs: 17-24) or <IGF-1R> L31D11 (SEQ ID NOs: 41-48) (both are affinity matured HUMAB <IGF-1R> Clone 18 antibodies) and b) humanized <EGFR>ICR62 (SEQ ID NOs: 1-8; see also WO 2006/082515 abbreviated as <EGFR>ICR62).

In a further embodiment said bispecific antibody is characterized in that the constant region derived of human origin.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda). Unless otherwise specified herein, numbering of amino acid residues in the Fc region or constant region is according to the EU numbering system, also called the EU index, as described in Kabat, E. A., et al., Sequences of Proteins of Immunological Interest, 5th ed., Public Health Service, National Institutes of Health, Bethesda, Md. (1991), NIH Publication 91-3242.

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see Kabat, E. A., et al., Sequences of Proteins of Immunological Interest, 5th ed., Public Health Service, National Institutes of Health, Bethesda, Md. (1991), NIH Publication 91-3242; e.g. Johnson, G. and Wu, T. T., Nucleic Acids Res. 28 (2000) 214-218; Kabat, E. A., et al., Proc. Natl. Acad. Sci. USA 72 (1975) 2785-2788). While antibodies of the IgG4 subclass show reduced Fc receptor (Fc gamma RIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment the bispecific antibody according to the invention comprises a constant region derived from human origin and is characterized in that the constant region is of human IgG subclass.

In one embodiment the bispecific antibody according to the invention comprises a constant region derived from human origin and is characterized in that the constant region is of human IgG1 subclass.

In one embodiment the bispecific antibody according to the invention comprises a constant region derived from human origin and is characterized in that the constant region is of human IgG2 subclass.

In one embodiment the bispecific antibody according to the invention comprises a constant region derived from human origin and is characterized in that the constant region is of human IgG3 subclass.

In one embodiment the bispecific antibody according to the invention comprises a constant region derived from human origin and is characterized in that the constant region is of human IgG4 subclass.

Typical human constant regions are shown in SEQ ID NO: 77-81.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat, supra).

The term "antibody-dependent cellular cytotoxicity (ADCC)" refers to lysis of human target cells by an antibody according to the invention in the presence of effector cells. ADCC is measured preferably by the treatment of a preparation of IGF-1R and EGFR expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

Cell-mediated effector functions of monoclonal antibodies can be enhanced by engineering their oligosaccharide component as described in Umana, P., et al., Nature Biotechnol. 17 (1999) 176-180, and U.S. Pat. No. 6,602,684. IgG1 type antibodies, the most commonly used therapeutic antibodies, are glycoproteins that have a conserved N-linked glycosylation site at Asn297 in each CH2 domain. The two complex biantennary oligosaccharides attached to Asn297 are buried between the CH2 domains, forming extensive contacts with the polypeptide backbone, and their presence is essential for the antibody to mediate effector functions such as antibody dependent cellular cytotoxicity (ADCC) (Lifely, M. R., et al., Glycobiology 5 (1995) 813-822; Jefferis, R., et al., Immunol. Rev. 163 (1998) 59-76; Wright, A., and Morrison, S. L., Trends Biotechnol. 15 (1997) 26-32). Umana, P., et al. Nature Biotechnol. 17 (1999) 176-180 and WO 99/54342 showed that overexpression in Chinese hamster ovary (CHO) cells of β(1,4)—N-acetylglucosaminyltransferase III ("GnTIII"), a glycosyltransferase catalyzing the formation of bisected oligosaccharides, significantly increases the in vitro ADCC activity of antibodies. Alterations in the composition of the Asn297 carbohydrate or its elimination affect also binding to FcγR and C1q (Umana, P., et al., Nature Biotechnol. 17 (1999) 176-180; Davies, J., et al., Biotechnol. Bioeng. 74 (2001) 288-294; Mimura, Y., et al., J. Biol. Chem. 276 (2001) 45539-45547; Radaev, S., et al., J. Biol. Chem. 276 (2001) 16478-16483; Shields, R. L., et al., J. Biol. Chem. 276 (2001) 6591-6604; Shields, R. L., et al., J. Biol. Chem. 277 (2002) 26733-26740; Simmons, L. C., et al., J. Immunol. Methods 263 (2002) 133-147).

Methods to enhance cell-mediated effector functions of monoclonal antibodies are reported e.g. in WO 2005/044859, WO 2004/065540, WO2007/031875, Umana, P., et al., Nature Biotechnol. 17 (1999) 176-180, WO 99/54342, WO 2005/018572, WO 2006/116260, WO 2006/114700, WO 2004/065540, WO 2005/011735, WO 2005/027966, WO 1997/028267, US 2006/0134709, US 2005/0054048, US 2005/0152894, WO 2003/035835 and WO 2000/061739 or e.g. in Niwa, R., et al., J. Immunol. Methods 306 (2005) 151-160; Shinkawa, T., et al, J. Biol. Chem. 278 (2003) 3466-3473; WO 03/055993 and US2005/0249722.

Therefore in one embodiment of the invention, the bispecific antibody is glycosylated (if it comprises an Fc part of IgG1 or IgG3) with a sugar chain at Asn297 (Numbering according to Kabat) whereby the amount of fucose within said sugar chain is 65% or lower. In another embodiment is the amount of fucose within said sugar chain is between 5% and 65%, in one embodiment between 20% and 50%. In another embodiment is the amount of fucose within said sugar chain is between 0% and 5%. "Asn297" according to the invention means amino acid asparagine located at about position 297 in the Fc region (Numbering according to Kabat). Based on minor sequence variations of antibodies, Asn297 can also be located some amino acids (usually not more than ±3 amino acids) upstream or downstream of position 297, i.e. between position 294 and 300.

In one embodiment the glycosylated antibody according to the invention the IgG subclass is of human IgG1 subclass or of IgG3 subclass. In a further embodiment the amount of N-glycolylneuraminic acid (NGNA) is 1% or less and/or the amount of N-terminal alpha-1,3-galactose is 1% or less within said sugar chain. The sugar chain show preferably the characteristics of N-linked glycans attached to Asn297 of an antibody recombinantly expressed in a CHO cell.

The term "the sugar chains show characteristics of N-linked glycans attached to Asn297 of an antibody recombinantly expressed in a CHO cell" denotes that the sugar chain at Asn297 of the constant region of the bispecific antibody according to the invention has the same structure and sugar residue sequence except for the fucose residue as those of the same antibody expressed in unmodified CHO cells, e.g. as those reported in WO 2006/103100.

The term "NGNA" as used within this application denotes the sugar residue N-glycolylneuraminic acid.

Glycosylation of human IgG1 or IgG3 occurs at Asn297 as core fucosylated biantennary complex oligosaccharide glycosylation terminated with up to two Gal residues.

Human constant heavy chain regions of the IgG1 or IgG3 subclass are reported in detail by Kabat, E. A., et al., Sequences of Proteins of Immunological Interest, 5th ed. Public Health Service, National Institutes of Health, Bethesda, Md. (1991) NIH Publication No 91-3242, and by Brüggemann, M., et al., J. Exp. Med. 166 (1987) 1351-1361; Love, T. W., et al., Methods Enzymol. 178 (1989) 515-527. These structures are designated as G0, G1 ($\alpha$-1,6- or $\alpha$-1,3-), or G2 glycan residues, depending from the amount of terminal Gal residues (Raju, T. S., Bioprocess Int. 1 (2003) 44-53). CHO type glycosylation of antibody Fc parts is e.g. described by Routier, F. H., Glycoconjugate J. 14 (1997) 201-207. Antibodies which are recombinantly expressed in non-glycomodified CHO host cells usually are fucosylated at Asn297 in an amount of at least 85%. The modified oligosaccharides of the constant region of the bispecific antibody according to the invention may be hybrid or complex. Preferably the bisected, reduced/not-fucosylated oligosaccharides are hybrid. In another embodiment, the bisected, reduced/not-fucosylated oligosaccharides are complex.

According to the invention "amount of fucose" means the amount of said sugar within the sugar chain at Asn297, related to the sum of all glycostructures attached to Asn297 (e.g. complex, hybrid and high mannose structures) measured by reverse phase UPLC (RP-UPLC and calculated as average value as described in Example 9. For the quantification of the relative levels of nonFuc content of the samples, the areas of all peaks representing oligosaccharides without fucose were summarized and related to the total peak area of all oligosaccharide peaks.

For all bispecific antibodies according to the invention, "GE" means glycoengineered and "WT" (wild type) means not glycoengineered.

In one further aspect of the invention the bispecific antibody according to the invention is an antibody with ADCC and/or CDC, and has a constant region of IgG1 or IgG3 (preferably IgG1) subclass from human origin which does bind Fc-gamma receptor and/or complement factor C1q. Such an antibody which does bind Fc receptor and/or complement factor C1q does elicit antibody-dependent cellular cytotoxicity (ADCC) and/or complement dependent cytotoxicity (CDC).

Recombinant Methods and Compositions

Antibodies may be produced using recombinant methods and compositions, e.g., as described in U.S. Pat. No. 4,816,567. In one embodiment, isolated nucleic acid encoding a bispecific antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of an anti-EGFR/ anti IGF-1R is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-EGFR/anti IGF-1R, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237, U.S. Pat. No. 5,789,199, and U.S. Pat. No. 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L., et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P., et al., Annals N.Y. Acad. Sci. 383 (1982) 44-68; MRC 5 cells; and FS4 cells. Other useful mammalian host cell lines include Chinese hamster ovary (CHO) cells, including DHFR—CHO cells (Urlaub, G., et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

The bispecific antibody according to the invention is produced by recombinant means. Thus, one aspect of the current invention is a nucleic acid encoding the antibody according to the invention and a further aspect is a host cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or E. coli cells, and the antibody is recovered from the cells (supernatant or cells after lysis). General methods for recombinant production of antibodies are well-known in the state of the art and described, for example, in the review articles of Makrides, S.C., Protein Expr. Purif. 17 (1999) 183-202; Geisse, S., et al., Protein Expr. Purif. 8 (1996) 271-282; Kaufman, R. J., Mol. Biotechnol. 16 (2000) 151-160; Werner, R. G., Drug Res. 48 (1998) 870-880.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Expression in NS0 cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 E9 (2002). Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

An antibody according to the invention with a reduced amount of fucose can be expressed in a glycomodified host cell engineered to express at least one nucleic acid encoding a polypeptide having GnTIII activity and a polypeptide having ManII activity in an amount to fucosylate according to the invention the oligosaccharides in the Fc region. In one embodiment, the polypeptide having GnTIII activity is a fusion polypeptide. Alternatively α1,6-fucosyltransferase activity of the host cell can be decreased or eliminated according to U.S. Pat. No. 6,946,292 to generate glycomodified host cells. The amount of antibody fucosylation can be predetermined e.g. either by fermentation conditions or by combination of at least two antibodies with different fucosylation amount.

The antibody according to the invention with a reduced amount of fucose can be produced in a host cell by a method comprising: (a) culturing a host cell engineered to express at least one polynucleotide encoding a fusion polypeptide having GnTIII activity and/or ManII activity under conditions which permit the production of said antibody and which permit fucosylation of the oligosaccharides present on the Fc region of said antibody in an amount according to the invention; and (b) isolating said antibody. In one embodiment, the polypeptide having GnTIII activity is a fusion polypeptide, preferably comprising the catalytic domain of GnTIII and the Golgi localization domain of a heterologous Golgi resident polypeptide selected from the group consisting of the localization domain of mannosidase II, the localization domain of β(1,2)—N-acetylglucosaminyltransferase I ("GnTI"), the localization domain of marmosidase I, the localization domain of β(1,2)—N-acetylglucosaminyltransferase II ("GnTII"), and the localization domain of α-1,6 core fucosyltransferase. Preferably, the Golgi localization domain is from mannosidase II or GnTI.

As used herein, a "polypeptide having GnTIII activity" refers to polypeptides that are able to catalyze the addition of an N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β-1,4-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependence in a given activity as compared to the GnTIII (i.e. the candidate polypeptide will exhibit greater activity or not more than about 25-fold less and, preferably, not more than about tenfold less activity, and most preferably, not more than about three-fold less activity relative to the GnTIII). As used herein, the term "Golgi localization domain" refers to the amino acid sequence of a Golgi resident polypeptide which is responsible for anchoring the polypeptide in location within the Golgi complex. Generally, localization domains comprise amino terminal "tails" of an enzyme.

For the production of antibodies according to the invention with a reduce amount of fucose likewise a host cell that is able and engineered to allow the production of an antibody with modified glycoforms can be used. Such a host cell has been further manipulated to express increased levels of one or more polypeptides having GnTIII activity. CHO cells are preferred as such host cells. Likewise cells producing antibody compositions with increased ADCC as reported in U.S. Pat. No. 6,946,292.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., (eds.) Current Protocols in Molecular Biology, Greene Publishing and Wiley Interscience, New York (1987). Different methods are well established and widespread used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)— and Cu(II)-affinity material), size exclusion chromatography, and electrophoretical methods (such as gel electrophoresis, capillary electrophoresis) (Vijayalakshmi, M., A., Appl. Biochem. Biotech. 75 (1998) 93-102).

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., and Van der Eb, A. J., Virology 52 (1973) 456-467. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S, N., et al, PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S., et al., J. Chromatogr. B 848 (2007) 79-87.

Immunoconjugates

The invention also provides immunoconjugates comprising an anti-EGFR/anti-IGF-1R bispecific antibody according to the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

In one embodiment, an immunoconjugate is an antibody-drug conjugate (ADC) in which an antibody is conjugated to one or more drugs, including but not limited to a maytansinoid (see U.S. Pat. No. 5,208,020, U.S. Pat. No. 5,416,064 and EP 0 425 235 B1); an auristatin such as monomethyl auristatin drug moieties DE and DF (MMAE and MMAF) (see U.S. Pat. No. 5,635,483, U.S. Pat. No. 5,780,588, and U.S. Pat. No. 7,498,298); a dolastatin; a calicheamicin or derivative thereof (see U.S. Pat. No. 5,712,374, U.S. Pat. No. 5,714,586, U.S. Pat. No. 5,739,116, U.S. Pat. No. 5,767,285, U.S. Pat. No. 5,770,701, U.S. Pat. No. 5,770,710, U.S. Pat. No. 5,773,001, and U.S. Pat. No. 5,877,296; Hinman, L. M., et al., Cancer Res. 53 (1993) 3336-3342; and Lode, H. N., et al., Cancer Res. 58 (1998) 2925-2928); an anthracycline such as daunomycin or doxorubicin (see Kratz, F., et al., Curr. Med. Chem. 13 (2006) 477-523; Jeffrey, S. C., et al., Bioorg. Med. Chem. Lett. 16 (2006) 358-362; Torgov, M. Y., et al., Bioconjug. Chem. 16 (2005) 717-721; Nagy, A., et al., Proc. Natl. Acad. Sci. USA 97 (2000) 829-834; Dubowchik, G. M., et al., Bioorg. & Med. Chem. Letters 12 (2002) 1529-1532; King, H. D., et al., J. Med. Chem. 45 (2002) 4336-4343; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include At211, I131, I125, Y90, Re186, Re188, Sm153, Bi212, P32, Pb212 and radioactive isotopes of Lu. When the radioconjugate is used for detection, it may comprise a radioactive atom for scintigraphic studies, for example TC99m or I123, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta, E. S., et al., Science 238 (1987) 1098-1104. Carbon-14-labeled 1-isothiocyanatobenzyl-3-methyldiethylene triamine pentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari, R. V., et al., Cancer Res. 52 (1992) 127-131; U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

Methods and Compositions for Diagnostics and Detection

In certain embodiments, an anti-EGFR/anti-IGF-1R bispecific antibody provided herein is useful for detecting the presence of EGFR and/or IGF-1R in a biological sample. The term "detecting" as used herein encompasses quantitative or qualitative detection. In certain embodiments, a biological sample comprises a cell or tissue, such as tumor tissues.

In one embodiment, an anti-EGFR/anti-IGF-1R bispecific antibody according to the invention for use in a method of diagnosis or detection is provided. In a further aspect, a method of detecting the presence of EGFR and/or IGF-1R in a biological sample is provided. In certain embodiments, the method comprises contacting the biological sample with an anti-EGFR/anti-IGF-1R bispecific antibody as described herein under conditions permissive for binding of the anti an anti-EGFR/anti-IGF-1R bispecific antibody according to the invention to EGFR and/or IGF-1R, and detecting whether a complex is formed between the anti an anti-EGFR/anti-IGF-1R bispecific antibody and EGFR and/or IGF-1R. Such method may be an in vitro or in vivo method. In one embodiment, an anti-EGFR/anti-IGF-1R bispecific antibody according to the invention is used to select subjects eligible for therapy with an anti-EGFR/anti-IGF-1R bispecific antibody, e.g. where EGFR and/or IGF-1R is a biomarker for selection of patients.

Exemplary disorders that may be diagnosed using an antibody of the invention include cancers.

In certain embodiments, labeled anti-EGFR/anti-IGF-1R bispecific antibody are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Pharmaceutical Formulations

Pharmaceutical formulations of a bispecific antibody as provided herein are prepared by mixing such antibody having the desired degree of purity with one or more optional pharmaceutically acceptable carriers (Remington's Pharmaceutical Sciences, 16th edition, Osol, A. (ed.) (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyl dimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as poly(vinylpyrrolidone); amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rhuPH20 (HYLENEX®, Baxter International, Inc.). Certain exemplary sHASEGPs and methods of use, including rhuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methyl methacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, 16th edition, Osol, A. (ed.) (1980). Sustained-release preparations may be prepared. Suitable examples of sustained-release preparations include semi-permeable matrices of solid hydrophobic polymers containing the antibody, which matrices are in the form of shaped articles, e.g. films, or microcapsules.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The formulations to be used for in vivo administration are generally sterile. Sterility may be readily accomplished, e.g., by filtration through sterile filtration membranes.

One embodiment of the invention is a pharmaceutical formulation comprising a bispecific antibody according to the invention.

Therapeutic Methods and Compositions

Any of the bispecific antibodies provided herein may be used in therapeutic methods.

In one aspect, a bispecific anti-EGFR/anti-IGF-1R antibody for use as a medicament is provided. In further aspects, a bispecific anti-EGFR/anti-IGF-1R antibody for use in treating cancer is provided. In certain embodiments, a bispecific anti-EGFR/anti-IGF-1R antibody for use in a method of treatment is provided. In certain embodiments, the invention provides a bispecific anti-EGFR/anti-IGF-1R antibody for use in a method of treating an individual having cancer comprising administering to the individual an effective amount of the bispecific anti-EGFR/anti-IGF-1R antibody. In one such embodiment, the method further comprises administering to the individual an effective amount of at least one additional therapeutic agent, e.g., as described below. In further embodiments, the invention provides a bispecific anti-EGFR/anti-IGF-1R antibody for use in inhibiting cell proliferation, especially cancer cell proliferation. In certain embodiments, the invention provides a bispecific anti-EGFR/anti-IGF-1R antibody for use in a method of inhibiting cell proliferation, especially cancer cell proliferation, in an individual comprising administering to the individual an effective of the bispecific anti-EGFR/anti-IGF-1R antibody to inhibit cell proliferation, especially cancer cell proliferation. An "individual" according to any of the above embodiments is preferably a human.

In a further aspect, the invention provides for the use of a bispecific anti-EGFR/anti-IGF-1R antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below. In a further embodiment, the medicament is for inhibiting cell proliferation, especially cancer cell proliferation. In a further embodiment, the medicament is for use in a method of inhibiting cell proliferation, especially cancer cell proliferation in an individual comprising administering to the individual an amount effective of the medicament to inhibit cell proliferation, especially cancer cell proliferation. An "individual" according to any of the above embodiments may be a human. In one embodiment, an "individual" is a human.

In one embodiment of the invention the bispecific antibodies according to the invention inhibit the IGF-1R phosphorylation and EGFR phosphorylation (see Example 4). In one embodiment the bispecific antibodies according to the invention inhibit IGF-1R phosphorylation in A549 cancer cells with an IC50 of 0.10 nM or lower. In one embodiment the bispecific antibodies according to the invention inhibit IGF-1R phosphorylation in BxPC3 cancer cells with an IC50 of 0.10 nM or lower. In one embodiment the bispecific antibodies according to the invention inhibit IGF-1R phosphorylation in TC-71 cancer cells with an IC50 of 0.10 nM or lower. In one embodiment the bispecific antibodies according to the invention inhibit EGFR phosphorylation in A549 cancer cells with an IC50 of 0.23 nM or lower. In one embodiment the bispecific antibodies according to the invention inhibit EGFR phosphorylation in BxPC3 cancer cells with an IC50 of 0.90 nM or lower.

In one embodiment of the invention the bispecific antibodies according to the invention inhibit the cancer cell proliferation or tumor cell proliferation (see Example 5). In one embodiment the bispecific antibodies according to the invention inhibit proliferation of A549 cancer cells with an IC50 of 0.20 nM or lower (preferably with an IC50 of 0.15 nM or lower). In one embodiment the bispecific antibodies according to the invention inhibit proliferation of RD-ES cancer cells with an IC50 of 0.10 nM or lower (preferably with an IC50 of 0.05 nM or lower).

In one embodiment of the invention the bispecific antibodies according to the invention are glycoengineered with an amount of fucose of 65% or lower (preferably between 50 and 5%) and induce ADCC in cancer cells (see Example 7). In one embodiment of the invention the bispecific antibodies according to the invention are glycoengineered with an amount of fucose of 65% or lower (preferably between 50 and 5%) and induce ADCC in H460M2 cancer cells with an EC50 of 0.10 nM or lower. In one embodiment of the invention the bispecific antibodies according to the invention are glycoengineered with an amount of fucose of 65% or lower (preferably between 50 and 5%) and induce ADCC in H322M cancer cells with an EC50 of 0.15 nM or lower.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewing's sarcoma, including refractory versions of any of the above cancers, or a combination of one or more of the above cancers.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "effective amount" of an agent, e.g., a pharmaceutical formulation, refers to an amount effective, at dosages and for periods of time necessary, to achieve the desired therapeutic or prophylactic result.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

In a further aspect, the invention provides pharmaceutical formulations comprising any of the bispecific antibodies provided herein, e.g., for use in any of the above therapeutic methods. In one embodiment, a pharmaceutical formulation comprises any of the bispecific antibodies provided herein and a pharmaceutically acceptable carrier. In another embodiment, a pharmaceutical formulation comprises any of the bispecific antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy. An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.5 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering e.g., an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-EGFR/anti-IGF-1R bispecific antibody according to the invention.

Another aspect of the invention is a bispecific antibody according to the invention for use in the treatment of cancer.

Another aspect of the invention is the use of a bispecific antibody according to the invention for the manufacture of a medicament for the treatment of cancer.

Another aspect of the invention is method of treatment of patient suffering from cancer by administering a bispecific antibody according to the invention to a patient in the need of such treatment.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The term "package insert" is used to refer to instructions customarily included in commercial packages of therapeutic products, that contain information about the indications, usage, dosage, administration, combination therapy, contraindications and/or warnings concerning the use of such therapeutic products.

It is understood that any of the above articles of manufacture may include an immunoconjugate of the invention in place of or in addition to an anti-EGFR/anti-IGF-1R bispecific antibody according to the invention.

Description of the Sequences a) Amino Acid Sequences:

SEQ ID NO: 1 heavy chain CDR1, humanized <EGFR>ICR62

SEQ ID NO: 2 heavy chain CDR2, humanized <EGFR>ICR62

SEQ ID NO: 3 heavy chain CDR3, humanized <EGFR>ICR62

SEQ ID NO: 4 light chain CDR1, humanized <EGFR>ICR62

SEQ ID NO: 5 light chain CDR2, humanized <EGFR>ICR62

SEQ ID NO: 6 light chain CDR3, humanized <EGFR>ICR62

SEQ ID NO: 7 heavy chain variable domain, humanized <EGFR>ICR62-I-HHD

SEQ ID NO: 8 light chain variable domain, humanized <EGFR>ICR62-I-KC

SEQ ID NO: 9 heavy chain CDR1, <IGF-1R> HUMAB-Clone 18

SEQ ID NO: 10 heavy chain CDR2, <IGF-1R> HUMAB-Clone 18

SEQ ID NO: 11 heavy chain CDR3, <IGF-1R> HUMAB-Clone 18

SEQ ID NO: 12 light chain CDR1, <IGF-1R> HUMAB-Clone 18

SEQ ID NO: 13 light chain CDR2, <IGF-1R> HUMAB-Clone 18

SEQ ID NO: 14 light chain CDR3, <IGF-1R> HUMAB-Clone 18

SEQ ID NO: 15 heavy chain variable domain, <IGF-1R> HUMAB-Clone 18

SEQ ID NO: 16 light chain variable domain, <IGF-1R> HUMAB-Clone 18

SEQ ID NO: 17 heavy chain CDR1, <IGF-1R> F13B5 (modified <IGF-1R> HUMAB-Clone 18)

SEQ ID NO: 18 heavy chain CDR2, <IGF-1R> F13B5

SEQ ID NO: 19 heavy chain CDR3, <<IGF-1R> F13B5

SEQ ID NO: 20 light chain CDR1, <IGF-1R> F13B5

SEQ ID NO: 21 light chain CDR2, <IGF-1R> F13B5

SEQ ID NO: 22 light chain CDR3, <<IGF-1R> F13B5

SEQ ID NO: 23 heavy chain variable domain, <IGF-1R> F13B5

SEQ ID NO: 24 light chain variable domain, <IGF-1R> F13B5

SEQ ID NO: 25 heavy chain CDR1, <IGF-1R> L37F7 (modified <IGF-1R> HUMAB-Clone 18)

SEQ ID NO: 26 heavy chain CDR2, <IGF-1R> L37F7

SEQ ID NO: 27 heavy chain CDR3, <<IGF-1R> L37F7

SEQ ID NO: 28 light chain CDR1, <IGF-1R> L37F7

SEQ ID NO: 29 light chain CDR2, <IGF-1R> L37F7

SEQ ID NO: 30 light chain CDR3, <IGF-1R> L37F7

SEQ ID NO: 31 heavy chain variable domain, <IGF-1R> L37F7
SEQ ID NO: 32 light chain variable domain, <IGF-1R> L37F7
SEQ ID NO: 33 heavy chain CDR1, <IGF-1R> L39D7 (modified <IGF-1R> HUMAB-Clone 18)
SEQ ID NO: 34 heavy chain CDR2, <IGF-1R> L39D7
SEQ ID NO: 35 heavy chain CDR3, <<IGF-1R> L39D7
SEQ ID NO: 36 light chain CDR1, <IGF-1R> L39D7
SEQ ID NO: 37 light chain CDR2, <IGF-1R> L39D7
SEQ ID NO: 38 light chain CDR3, <IGF-1R> L39D7
SEQ ID NO: 39 heavy chain variable domain, <IGF-1R> L39D7
SEQ ID NO: 40 light chain variable domain, <IGF-1R> L39D7
SEQ ID NO: 41 heavy chain CDR1, <IGF-1R> L31D11 (modified <IGF-1R> HUMAB-Clone 18)
SEQ ID NO: 42 heavy chain CDR2, <IGF-1R> L31D11
SEQ ID NO: 43 heavy chain CDR3, <<IGF-1R> L31D11
SEQ ID NO: 44 light chain CDR1, <IGF-1R> L31D11
SEQ ID NO: 45 light chain CDR2, <IGF-1R> L31D11
SEQ ID NO: 46 light chain CDR3, <IGF-1R> L31D11
SEQ ID NO: 47 heavy chain variable domain, <IGF-1R> L31D11
SEQ ID NO: 48 light chain variable domain, <IGF-1R> L31D11
SEQ ID NO: 49 heavy chain CDR1, <IGF-1R> L31D7 (modified <IGF-1R> HUMAB-Clone 18)
SEQ ID NO: 50 heavy chain CDR2, <IGF-1R> L31D7
SEQ ID NO: 51 heavy chain CDR3, <<IGF-1R> L31D7
SEQ ID NO: 52 light chain CDR1, <IGF-1R> L31D7
SEQ ID NO: 53 light chain CDR2, <IGF-1R> L31D7
SEQ ID NO: 54 light chain CDR3, <IGF-1R> L31D7
SEQ ID NO: 55 heavy chain variable domain, <IGF-1R> L31D7
SEQ ID NO: 56 light chain variable domain, <IGF-1R> L31D7
SEQ ID NO: 57 OA-F13B5-scFab-GA201 Heavy chain 1
SEQ ID NO: 58 OA-F13B5-scFab-GA201 Heavy chain 2
SEQ ID NO: 59 OA-F13B5-scFab-GA201 Light chain
SEQ ID NO: 60 OA-L31D11-scFab-GA201 Heavy chain 1
SEQ ID NO: 61 OA-L31D11-scFab-GA201 Heavy chain 2
SEQ ID NO: 62 OA-L31D11-scFab-GA201 Light chain
SEQ ID NO: 63 CM-F13B5-GA201 Heavy chain 1
SEQ ID NO: 64 CM-F13B5-GA201 Heavy chain 2
SEQ ID NO: 65 CM-F13B5-GA201 Light chain 1
SEQ ID NO: 66 CM-F13B5-GA201 Light chain 2
SEQ ID NO: 67 CM-L31D11-GA201 Heavy chain 1
SEQ ID NO: 68 CM-L31D11-GA201 Heavy chain 2
SEQ ID NO: 69 CM-L31D11-GA201 Light chain 1
SEQ ID NO: 70 CM-L31D11-GA201 Light chain 2
SEQ ID NO: 71 Tv-F13B5-GA201 chain 1
SEQ ID NO: 72 Tv-F13B5-GA201 chain 2
SEQ ID NO: 73 Tv-L31D11-GA201 chain 1
SEQ ID NO: 74 Tv-L31D11-GA201 chain 2
SEQ ID NO: 75 Human EGFR
SEQ ID NO: 76 Human IGF-1R
SEQ ID NO:77 Human kappa constant light chain region
SEQ ID NO:78 Human lambda constant light chain region
SEQ ID NO:79 Human constant heavy chain region IgG1 (Caucasian Allotype)
SEQ ID NO:80 Human constant heavy chain region IgG1 (Afroamerican Allotype)
SEQ ID NO:81 Human constant heavy chain region IgG4
b) Nucleic Acid Sequences:
SEQ ID NO: 82 Library template for Aid 8 VL and VH library (pRJH61)
SEQ ID NO: 83 Library primer sequences AM_VL_AK18_L1_ba
SEQ ID NO: 84 Library primer sequences AM_VL_AK18_L2_fo
SEQ ID NO: 85 Library primer sequences AM_VH_AK18_H1_ba
SEQ ID NO: 86 Library primer sequences AM_VH_AK18_H2_fo The following examples, sequence listing and figures are provided to aid the understanding of the present invention, the true scope of which is set forth in the appended claims. It is understood that modifications can be made in the procedures set forth without departing from the spirit of the invention.

EXPERIMENTAL PROCEDURE

Examples

Materials & Methods

Recombinant DNA Techniques

Standard methods were used to manipulate DNA as described in Sambrook, J., et al., Molecular Cloning: A Laboratory Manual; Cold Spring Harbor Laboratory Press, Cold Spring Harbor, N.Y., (1989). The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A., et al., Sequences of Proteins of Immunological Interest, 5th ed., Public Health Service, (1991) NIH Publication No 91-3242. Amino acids of antibody chains are numbered according to EU numbering (Edelman, G. M., et al., PNAS 63 (1969) 78-85; Kabat, E. A., et al., Sequences of Proteins of Immunological Interest, 5th ed., Public Health Service (1991) NIH Publication No 91-3242). The GCG's (Genetics Computer Group, Madison, Wis.) software package version 10.2 and Infomax's Vector NTI Advance suite version 8.0 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments encoding heavy or light chains with C-terminal attachment of scFv antibody fragments, "knobs-into-hole" antibody heavy chains carrying S354C and T366W mutations and "knobs-into-hole" heavy chains carrying Y349C, T366S, L368A and Y407V mutations in the CH3 domain in combination with unmodified VH domains, crossed C kappa domains or scFab antibody fragments as well as unmodified antibody light chains or CH1 domain exchanged light chains are flanked by singular restriction endonuclease cleavage sites (BamHI—XbaI, BamHI—XmnI or BamHI—KpnI) and were cloned into pGA18 (ampR) plasmids. The plasmid DNA was purified from transformed bacteria and concentration determined by UV spectroscopy. The DNA sequence of the subcloned gene fragments was confirmed by DNA sequencing. All constructs were designed with a 5'-end DNA sequence coding for a leader peptide (MGWSCIILFL-VATATGVHS), which targets proteins for secretion in eukaryotic cells.

Construction of the Expression Plasmids

A Roche expression vector was used for the construction of all "knobs-into-hole" heavy chain as well as antibody light chain encoding expression plasmids. The vector is composed of the following elements:

- a hygromycin resistance gene as a selection marker,
- an origin of replication, oriP, of Epstein-Barr virus (EBV),
- an origin of replication from the vector pUC 18 which allows replication of this plasmid in E. coli
- a beta-lactamase gene which confers ampicillin resistance in E. coli,
- the immediate early enhancer and promoter from the human cytomegalovirus (HCMV),
- the human 1-immunoglobulin polyadenylation ("poly A") signal sequence, and
- unique BamHI and XbaI restriction sites.

The immunoglobulin genes comprising heavy or light chains with C-terminal attachment of scFv antibody fragments, "knobs-into-hole" heavy chains with unmodified VH domains, crossed C kappa domains or scFab fragments as well as unmodified light chains or CH1 domain exchanged light chains were prepared by gene synthesis and cloned into pGA18 (ampR) plasmids as described. The pG18 (ampR) plasmids carrying the synthesized DNA segments and the Roche expression vector were digested with BamHI and XbaI, BamHI and XmnI or BamHI and KpnI restriction enzymes (Roche Molecular Biochemicals) and subjected to agarose gel electrophoresis. Purified heavy or light chains with C-terminal attachment of scFv antibody fragments, "knobs-into-hole" heavy and unmodified or domain exchanged light chain encoding DNA segments were then ligated to the isolated Roche expression vector BamHI/XbaI, BamHI/XmnI or BamHI/KpnI fragment resulting in the final expression vectors. The final expression vectors were transformed into E. coli cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and sequence integrity confirmed by DNA sequencing.

Transient Expression of Bispecific Antibodies in HEK293 Cells

Recombinant bispecific antibodies were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1 \times 10^6$ viable cells/ml one day before transfection. For transfection, DNA was prepared in 10 ml Dulbecco's PBS (PAA, Austria) using 162.5 µA of 293-Free™ Transfection Reagent (Merck, USA) and 125 µg of heavy or light chain with C-terminal attachment of scFv encoding DNA in a plasmid ratio of 1:1 or "Knobs-into-hole" heavy chain 1 and 2 and light chain plasmid DNA in a 1:2:1 or 1:3:1 molar ratio in 250 ml final transfection volume. For transfection of Cross Mabs, a plasmid ratio of 1:1:2:2 or 1:1:3:2 of "Knobs-into-hole" heavy chain 1:unmodified light chain:C kappa domain exchanged "Knobs-into-hole" heavy chain 2:CH1 domain exchanged light chain was prepared. Antibody containing cell culture supernatants were harvested 7 days after transfection by centrifugation at 14000 g for 30 minutes and filtered through a sterile filter (0.22 µm). Supernatants were stored at −20° C. until purification.

Purification of Bispecific Antibodies

Bispecific antibodies were purified from cell culture supernatants by affinity chromatography using MabSelect-Sure-Sepharose™ (GE Healthcare, Sweden) and Superdex 200 size exclusion (GE Healthcare, Sweden) chromatography. Briefly, sterile filtered cell culture supernatants were captured on a MabSelect SuRe resin equilibrated with PBS buffer (10 mM $Na_2HPO_4$, 1 mM $KH_2PO_4$, 137 mM NaCl and 2.7 mM KCl, pH 7.4), washed with equilibration buffer and eluted with 25 mM sodium citrate at pH 3.0. The eluted protein fractions were pooled, neutralized with 2M Tris, pH 9.0 and further purified by size exclusion chromatography using a Superdex 200 26/60 GL (GE Healthcare, Sweden) column equilibrated with 20 mM histidine, 140 mM NaCl, pH 6.0. Size exclusion chromatography fractions were analysed by CE-SDS (Caliper Life Science, USA) and bispecific antibody containing fractions were pooled and stored at −80° C.

Analysis of Purified Proteins

The protein concentration of purified protein samples was determined by measuring the optical density (OD) at 280 nm, using the molar extinction coefficient calculated on the basis of the amino acid sequence. Purity, antibody integrity and molecular weight of bispecific and control antibodies were analyzed by CE-SDS using microfluidic Labchip technology (Caliper Life Science, USA). 5 µA of protein solution was prepared for CE-SDS analysis using the HT Protein Express Reagent Kit according manufacturer's instructions and analysed on LabChip GXII system using a HT Protein Express Chip. Data were analyzed using LabChip GX Software version 3.0.618.0. The aggregate content of bispecific and control antibody samples was analyzed by high-performance SEC using a Superdex 200 analytical size-exclusion column (GE Healthcare, Sweden) in 200 mM $KH_2PO_4$, 250 mM KCl, pH 7.0 running buffer at 25° C. 25 µg protein were injected on the column at a flow rate of 0.5 ml/min and eluted isocratic over 50 minutes. The integrity of the amino acid backbone of reduced bispecific antibody light and heavy chains was verified by NanoElectrospray Q-TOF mass spectrometry after removal of N-glycans by enzymatic treatment with Peptide-N-Glycosidase F (Roche Molecular Biochemicals).

Surface Plasmon Resonance

Standard kinetics were evaluated by fitting of the observed time course of surface plasmon resonance signals for the association and dissociation phase with a Langmuir 1:1 binding model with double referencing (against c=0 nM and FC1=blank surface) without local bulk effect (RI=0) by Biacore evaluation software.

Binding of Human and cyno IGF-1R to MAbs

Standard amine coupling according to the manufacturer's instructions onto Chip C1; running buffer HBS-N, T=25° C., activation by mixture of EDC/NHS; anti-huFc capture antibody was diluted in coupling buffer 10 nM NaAc, pH 4.5, c=1 µg/mL, and coupled with programmed target level 200RU (actual immobilization level on FC1-FC4~189-195RU); finally remaining activated carboxyl groups were blocked by injection of 1 M ethanolamine. Bispecific or parental antibodies were diluted to 1.3 nM in PBST +0.1% BSA and captured as ligand in separate cycles by injection with 10 µl/min for 30 sec. Capture levels 5.4-9.2RU. Three MAbs per run on FCs2-4, FC1 only capture antibody as reference. Kinetics of human and cyno IGF-1R binding as analyte was measured at 37° C., running buffer PBST. The analytes were injected in a series of 3fold increasing concentrations (1.65-400 nM in PBST+0.1% BSA) with flow rate 50 µl/min, 120 sec association, 600 sec dissociation. The capture antibody was regenerated after each cycle with 10 mM glycine pH 1.75/30 µl/min for 60 sec.

Binding of Human and Cyno EGFR to MAbs

Standard amine coupling according to the manufacturer's instructions onto Chip CM5; running buffer HBS-N, T=25° C., activation by mixture of EDC/NHS; anti-huFc capture antibody was diluted in coupling buffer 10 mM NaAc, pH 4.5, c=4 µg/mL, and coupled with programmed target level 1000RU (actual immobilization level on FC1-FC4 ~1170-1260RU); finally remaining activated carboxyl groups were blocked by injection of 1 M ethanolamine. Bispecific or parental antibodies were diluted to 10 nM in PBS+0.1% BSA and captured as ligand in separate cycles by injection with 10 µl/min for 30 sec. Capture levels 15-79RU. Three MAbs per run on FCs2-4, FC1 only capture antibody as reference. Kinetics of monomeric human HER1-ECD and cyno EGFR binding as analyte was measured at 37° C., running buffer PBS. The analytes were injected in a series of 3fold increasing concentrations (4.12-1000 nM in PBS+ 0.1% BSA) with flow rate 50 µl/min, 120 sec association, 1200 sec dissociation. The capture antibody was regenerated after each cycle with 10 mM glycine pH 1.75/30 µl/min for 60 sec.

Binding of Human and Cyno FcgRIIIa to MAbs

Standard amine coupling according to the manufacturer's instructions onto Chip C1; running buffer HBS-N, T=25° C., activation by mixture of EDC/NHS; monomeric huHER1-ECD was diluted in coupling buffer 10 mM NaAc, pH 4.5, c=30 µg/mL, and coupled with programmed target level 400RU (actual immobilization level on FC1-FC4 ~390-445RU); finally remaining activated carboxyl groups were blocked by injection of 1 M ethanolamine. Bispecific or parental antibodies were diluted to 20 nM in PBST+0.1% BSA and captured as ligand in separate cycles by injection with 10 µl/min for 60 sec. Three MAbs on FCs2-4, FC1 only capture antibody as reference. Kinetics of human FcgRIIIa (V158), huFcgRIIIa(F158) and cyno FcgRIIIa binding as analyte was measured at 25° C., running buffer PBST. The analytes were injected in a series of 3fold increasing concentrations (2.74-2000 nM in PBST+0.1% BSA) with flow rate 50 µl/min, 180 sec association, 900 sec dissociation. Free HER1-ECD was regenerated after each cycle with 15 mM NaOH/50 µl/min for 60 sec, followed by 180 sec stabilization period. In addition to Langmuir 1:1 fit analysis, steady state affinities were calculated from the R(equilibrium) as function of analyte concentration.

Simultaneous binding of huEGFR and huIGF-1R to MAbs

Standard amine coupling according to the manufacturer's instructions onto Chip C1; running buffer HBS-N, T=25° C., activation by mixture of EDC/NHS; anti-huFAB capture antibody was diluted in coupling buffer 10 mM NaAc, pH 5.0, c=50 µg/mL, and coupled with programmed target level 1000RU (actual immobilization level on FC1-FC4 ~955-1040RU); finally remaining activated carboxyl groups were blocked by injection of 1 M ethanolamine. Bispecific antibodies were diluted to 20 nM in PBST+0.1% BSA and captured as ligand in separate cycles by injection with 10 µl/min for 60 sec. Three MAbs on FCs2-4 per run, FC1 only capture antibody as reference. Binding of human EGFR and IGF-1R as analyte was measured at 25° C., running buffer PBST. The analytes were injected consecutively in 'dual inject' mode in concentration of 400 nM in PBST+0.1% BSA with flow rate 30 µl/min, 180 sec association, 600 sec dissociation. The sequence of the receptors was permutated in different cycles including blank buffer injects as control. The capture antibody was regenerated after each cycle with 10 mM glycine pH 2.1/30 µl/min for 60 sec.

Example 1

Construction of affinity maturation libraries based on anti-IGF-1R HUMAB Clone 18 (Ak18)

Affinity maturation libraries were constructed on basis of the Fab-fragment of <IGF-1R> HUMAB Clone 18 (DSM ACC 2587; WO 2005/005635, abbreviated as <IGF-1R>Clone18, <IGF-1R> AK18, see Sequences SEQ ID NOs: 9-16) that was cloned into a phagemid vector enabling subsequent phage display selections. More precisely, 2 sublibraries were constructed with randomized positions in CDR1 (residues 30, 31, 32, 34 according to Kabat numbering scheme) and CDR2 (residues 50, 51, 52, 53) of the light chain variable domain (Ak18 VL library) and randomized positions in CDR1 (residues 31, 32, 33, 34, 35) and CDR2 (residues 50, 52, 53, 54, 56, 58) of the heavy chain variable domain (Ak18 VH library), respectively. Randomized variable domains were PCR-amplified separately by using a randomized reverse primer over CDR1 and a randomized forward primer over CDR2. These were combined with respective outer primers to generate 2 PCR fragments per V-domain that were subsequently assembled by sequence homology in the 5' end constant parts of the library primers (e.g. reverse primer AM_VL_AK18_L1_ba annealing to forward primer AM_VL_AK18_L2_ fo). Assembly products were amplified by addition of the respective outer primers, digested NcoI/BsiWI (Aid 8 VL library) and AscI/SacII (Aid 8 VH library), respectively, and cloned into similarly digested acceptor vectors. Purified ligations were used for ~60 transformations per sublibrary into electrocompetent E. coli TG1 to obtain final library sizes of $1.4 \times 10^{10}$ for Ak18 VL library and $8.7 \times 10^9$ for Ak18 VH library with 65.3% and 73% functional clones, respectively. Phagemid particles displaying the Fab libraries were rescued and purified by PEG/NaCl precipitation to be used for selections.

Selection of Affinity-Matured Anti-IGF-1R mAbs Derived from Parental mAb Ak18

Selections against the extracellular domains of human and/or cynomolgus IGF-1R were carried out using a pool of Aid 8 VL and VH library phage. Three different selection strategies were carried out: 1. decrease of antigen concentration over subsequent rounds of bio-panning (ranging from 10 nM in the first selection round down to 0.8 nM in the third to fifth selection round), 2. competitive selection by addition of parental IgG Ak18 at 10-fold antigen concentration or by addition of 1 µM non-biotinylated human IGF-1R to the binding reactions (only in rounds where biotinylated cynomolgus IGF-1R was used as target) or 3. off-rate selections by allowing dissociation of phage-antibody:antigen complexes for either 3 hours or 3 days. Selections were carried out by either using only human or only cynomolgus IGF-1R during subsequent selection rounds or alternating between these two species to avoid affinity-maturation towards one species only. Selection outputs from bio-panning rounds 2-5 were screened by SPR using BioRad's ProteOn XPR36 to identify clones with superior kinetic rate constants and affinity compared to parental Ak18. VL and VH sequences of selected clones are shown in Table 1 below.

Screening of Selection Outputs by SPR (ProteOn XPR36)

Kinetic rate constants kon and koff as well as affinity (KD) of affinity-matured clones were measured by surface plasmon resonance (SPR) using a ProteOn XPR36 (BioRad) instrument at 25° C. applying a capture method for the Fab fragments. Briefly, anti-Fab capture antibody (Jackson ImmunoResearch, #109-005-006) was immobilized at high levels (9.000-10.000 RU) at 30 ul/min onto separate vertical channels of a GLM chip by simultaneously activating all channels for 5 min with a freshly prepared mixture of EDC and SNHS, and then injecting 24 ug/ml anti-Fab in 10 mM Na-acetate buffer pH 5.0 for 5 min. Channels were blocked using a 5-min injection of ethanolamine. Fab fragments of affinity-matured clones were either captured from bacterial culture supernatants or from purified protein preparations along the vertical channels for 100 s at 30 ul/min to achieve ligand densities of ~250 RU. In a one-shot kinetic assay set-up (OSK), human or cynomolgus IGF-1R were injected as analyte along the horizontal channels at 50 ul/min, association time 200 s, dissociation time 600 s in a three-fold dilution series ranging from 33-0.4 nM. Running buffer (PBST) was injected along the sixth channel to provide an "in-line" blank for referencing. Association rates (kon) and dissociation rates (koff) were calculated using a simple 1:1 Langmuir binding model (ProteOn Manager software version 2.1) by simultaneously fitting the association and dissociation sensorgrams. The equilibrium dissociation constant (KD) was calculated as the ratio koff/kon. Results are shown in Table 2 below.

```
Library template for Ak18 VL and VH library (pRJH61) (i.e.
complete Fab coding region comprising PelB leader sequence +
VL Ak18 + CL constant domain incl. c-myc and FLAG-tag for
light chain and PelB + VH Ak18 + CH1 constant domain
incl. His6-tag for heavy chain)
                                                 (SEQ ID NO: 82)
ATGAAATACCTATTGCCTACGGCAGCCGCTGGATTGTTATTACTCGCGGCCCAGCCGGCC
ATGGCCGAAATTGTTCTGACCCAGAGTCCGGCAACCCTGAGCCTGAGTCCGGGTGAACGT
GCAACCCTGTCTTGTCGTGCAAGCCAGAGCGTTAGTAGCTACCTGGCCTGGTATCAGCAG
AAACCGGGTCAGGCACCGCGTCTGCTGATTTATGATGCATCCAAGCGTGCAACCGGTATT
CCGGCACGTTTTAGCGGTAGCGGATCCGGCACCGATTTTACCCTGACCATTAGCAGCCTG
GAACCGGAAGATTTTGCCGTTTATTATTGTCAGCAGCGTAGCAAATGGCCTCCGTGGACC
TTTGGTCAGGGCACCAAAGTTGAAAGCAAACGTACGGTGGCTGCACCATCTGTCTTCATC
TTCCCGCCATCTGATGAGCAGTTGAAATCTGGAACTGCCTCTGTTGTGTGCCTGCTGAAT
AACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGC
ACCCTGACGCTGAGCAAAGCAGACTACGAGAAACACAAAGTCTACGCCTGCGAAGTCACC
CATCAGGGCCTGAGCTCGCCCGTCACAAAGAGCTTCAACAGGGGAGAGTGTGGAGCCGCA
GAACAAAAACTCATCTCAGAAGAGGATCTGAATGGAGCCGCAGACTACAAGGACGACGAC
GACAAGGGTGCCGCATAATAAGGCGCGCCAATTCTATTTCAAGGAGACAGTCATATGAAA
TACCTGCTGCCGACCGCTGCTGCTGGTCTGCTGCTCCTCGCTGCCCAGCCGGCGATGGCC
CAGGTTGAACTGGTTGAAAGCGGTGGTGGTGTTGTTCAGCCTGGTCGTAGCCAGCGTCTG
AGCTGTGCAGCATCCGGATTTACCTTTAGCAGCTATGGCATGCACTGGGTTCGTCAGGCA
CCGGGTAAAGGTCTGGAATGGGTTGCAATTATTTGGTTTGATGGAAGCAGTACCTACTAT
GCAGATAGCGTTCGTGGTCGTTTTACCATTAGCCGTGATAATAGCAAAAACACCCTGTAT
CTGCAGATGAATAGCCTGCGTGCAGAAGATACCGCAGTTTATTTTTGTGCACGTGAACTG
GGTCGTCGTTATTTTGATCTGTGGGGTCGTGGCACCCTGGTTAGCGTTAGCAGCGCTAGC
ACCAAAGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGGAAC
TCAGGCGCCCTGACCAGCGGCGTGCACACCTTCCCGGCTGTCCTACAGTCCTCAGGACTC
TACTCCCTCAGCAGCGTGGTGACCGTGCCCTCCAGCAGCTTGGGCACCCAGACCTACATC
TGCAACGTGAATCACAAGCCCAGCAACACCAAAGTGGACAAGAAAGTTGAGCCCAAATCT
TGTGACGCGGCCGCAAGCACTAGTGCCCATCACCATCACCATCACGCCGCGGCATAG Library primer sequences
AM_VL_AK18_L1_ba
                                                 (SEQ ID NO: 83)
TCAGCAGACGCGGTGCCTGACCCGGTTTCTGCTGATACCA GGC CAG ATA GCT GCT
                                          1        2   3   4
AACGCTCTGGCTTGCACGACAAGACAGG 1  60% template base + 40% N/+40% K/+40% M
2  70% template base + 30% N/+30% M
3  60% template base + 40% N/+40% M
4  60% template base + 40% N/+40% M AM_VL_AK18_L2_fo
                                                 (SEQ ID NO: 84)
CAGAAACCGGGTCAGGCACCGCGTCTGCTGATTTAT GAT GCG AGC AAA
                                     1   2   3   4
CGTGCAACCGGTATTCCGGCACGTTTTAG 1   60% template base + 40% N/+40% K
2  100% template base/70% template + 30% G
3  100% template base/70% template + 30% C
4   60% template base + 40% N/+40% V/+40% K AM_VH_AK18_H1_ba
                                                 (SEQ ID NO: 85)
CAACCCATTCCAGACCTTTACCCGGTGCCTGACGAACCCA ATG CAT ACC ATA AGA
                                         1   2   3   4   5
GCTAAAGGTAAATCCGGATGCTG 1  60% template base + 40% N
2 100% template base/60% C + 40% A
```

-continued
```
3  60% template base + 40% N/+40% M
4  60% template base + 40% N/+40% M
5  60% template base + 40% N/+40% B AM_VH_AK18_H2_fo
                                                       (SEQ ID NO: 86)
AGGCACCGGGTAAAGGTCTGGAATGGGTTGCA ATT ATT TGG TTT GAT GGC AGC
                                  1   2   3   4
TCT ACC TAT TATGCAGATAGCGTTCGTGGTC
 5      6

1  60% template base + 40% N/+40% K
2  60% template base + 40% N/+40% K
3  60% template base + 40% R/+40% V/+40% K
4  60% template base + 40% N/+40% V/+40% K
5  60% template base + 40% N/+40% K
6  60% template base + 40% N/+40% K
```

The IUPAC has designated the symbols for nucleotides. Apart from the five (A, G, C, T/U) bases, often degenerate bases are used especially for designing PCR primers. These nucleotide codes are listed here.

| IUPAC nucleotide code | Base |
|---|---|
| A | Adenine |
| C | Cytosine |
| G | Guanine |
| T (or U) | Thymine (or Uracil) |
| R | A or G |
| Y | C or T (U) |
| S | G or C |
| W | A or T (U) |
| K | G or T (U) |
| M | A or C |
| B | C or G or T (U) |
| D | A or G or T (U) |
| H | A or C or T (U) |
| V | A or C or G |
| N | any base |

Above described affinity maturation of the <IGF-1R> antigen binding site and subsequent selection resulted in the following <IGF-1R> antigen binding site comprising antibodies with at 10 fold increased KD-value of the binding affinity of the <IGF-1R> antigen binding site:

TABLE 1

Amino acid sequences of the variable light chain domain (VL) and variable heavy chain domain (VH) of affinity-matured <IGF-1R> antigen binding sites and of parental AK18

| VL | VH |
|---|---|
| F13B5 | F13B5 |
| EIVLTQSPATLSLSPGERATLSCR | QVELVESGGGVVQPGRSQRLSCA |
| ASQSVSSYLAWYQQKPGQAPRL | ASGFTFSSYGMHWVRQAPGKGL |
| LIYQASKRATGIPARFSGSGSGTD | EWVAIIWFDGSSTYYADSVRGRF |
| FTLTISSLEPEDFAVYYCQQRSKY | TISRDNSKNTLYLQMNSLRAEDTA |
| PPWTFGQGTKVESK | VYFCARELGRRYFDLWGRGTLVS |
|  | VSS |
| L37F7 | L37F7 |
| EIVLTQSPATLSLSPGERATLSCR | QVELVESGGGVVQPGRSQRLSCA |
| ASQSVSSQLAWYQQKPGQAPRL | ASGFTFSSYGMHWVRQAPGKGL |
| LIYKATNRATGIPARFSGSGSGT | EWVAIIWFDGSSTYYADSVRGRF |
| DFTLTISSLEPEDFAVYYCQQRSK | TISRDNSKNTLYLQMNSLRAEDTA |
| YPPWTFGQGTKVESK | VYFCARELGRRYFDLWGRGTLVS |
|  | VSS |

TABLE 1-continued

Amino acid sequences of the variable light chain domain (VL) and variable heavy chain domain (VH) of affinity-matured <IGF-1R> antigen binding sites and of parental AK18

| VL | VH |
|---|---|
| L39D7 | L39D7 |
| EIVLTQSPATLSLSPGERATLSCR | QVELVESGGGVVQPGRSQRLSCA |
| ASQSVSKQLAWYQQKPGQAPR | ASGFTFSSYGMHWVRQAPGKGL |
| LLIYNASKRATGIPARFSGSGSGT | EWVAIIWFDGSSTYYADSVRGRF |
| DFTLTISSLEPEDFAVYYCQQRSK | TISRDNSKNTLYLQMNSLRAEDTA |
| YPPWTFGQGTKVESK | VYFCARELGRRYFDLWGRGTLVS |
|  | VSS |
| L31D11 | L31D11 |
| EIVLTQSPATLSLSPGERATLSCR | QVELVESGGGVVQPGRSQRLSCA |
| ASRSVYSSLAWYQQKPGQAPRL | ASGFTFSSYGMHWVRQAPGKGL |
| LIYKASSRATGIPARFSGSGSGTD | EWVAIIWFDGSSTYYADSVRGRF |
| FTLTISSLEPEDFAVYYCQQRSK | TISRDNSKNTLYLQMNSLRAEDTA |
| WPPWTFGQGTKVESK | VYFCARELGRRYFDLWGRGTLVS |
|  | VSS |
| L31D7 | L31D7 |
| EIVLTQSPATLSLSPGERATLSCR | QVELVESGGGVVQPGRSQRLSCA |
| ASQSVIQSLAWYQQKPGQAPRL | ASGFTFSSYGMHWVRQAPGKGL |
| LIYRASKRATGIPARFSGSGSGT | EWVAIIWFDGSSTYYADSVRGRF |
| DFTLTISSLEPEDFAVYYCQQRS | TISRDNSKNTLYLQMNSLRAEDTA |
| KWPPWTFGQGTKVESK | VYFCARELGRRYFDLWGRGTLVS |
|  | VSS |
| Ak18 (HUMAB-Clone 18) | Ak18 (HUMAB-Clone 18) |
| EIVLTQSPATLSLSPGERATLSCR | QVELVESGGGVVQPGRSQRLSCA |
| ASQSVSSYLAWYQQKPGQAPRL | ASGFTFSSYGMHWVRQAPGKGL |
| LIYDASKRATGIPARFSGSGSGTD | EWVAIIWFDGSSTYYADSVRGRF |
| FTLTISSLEPEDFAVYYCQQRSK | TISRDNSKNTLYLQMNSLRAEDTA |
| WPPWTFGQGTKVESK | VYFCARELGRRYFDLWGRGTLVS |
|  | VSS |

TABLE 2

Binding affinity to human IGF-1R of the <IGF-1R> antigen binding sites of CDR-modified antibodies in comparison with parental AK18, and x-fold increase in binding affinity (which is calculated as the ratio KD (unmodified = parental)/KD (modified)

| Clones | Analyte | ka (1/Ms) | kd (1/s) | KD (mol/l) | x-fold increase of binding affinity (=KD (unmodified AK18)/KD (CDR-modified) |
|---|---|---|---|---|---|
| F13B5 | hu IGF-1R | 1.70E+05 | 2.50E−04 | 1.47E−09 | 12.45 |
| L37F7 | hu IGF-1R | 2.32E+05 | 2.37E−04 | 1.02E−09 | 17.94 |
| L39D7 | hu IGF-1R | 3.51E+05 | 2.70E−04 | 7.69E−10 | 23.80 |
| L31D11 | hu IGF-1R | 5.71E+05 | 1.53E−04 | 2.69E−10 | 68.03 |
| L31D7 | hu IGF-1R | 5.23E+05 | 5.38E−04 | 1.03E−09 | 17.77 |
| unmodified (parental) Ak18 | hu IGF-1R | 1.53E+05 | 2.71E−03 | 1.83E−08 | 1.00 |

TABLE 3

Modifications in CDRs of <IGF-1R> antigen binding sites with at least 10 fold increase binding affinity in comparison with parental, unmodified CDRs of AK18 (<IGF-1R>HUMAB Clone 18, see Sequences SEQ ID NOs: 9-14)

| Clone | $V_L$ CDR1 | $V_L$ CDR2 | $V_L$ CDR3 |
|---|---|---|---|
| L31D11 | RASRSVYSSLA | KASSRAT | QQRSKWPPWT |
| L37F7 | RASQSVSSQLA | KATNRAT | QQRSKYPPWT |
| F13B5 | RASQSVSSYLA | QASKRAT | QQRSKYPPWT |
| L39D7 | RASQSVSKQLA | NASKRAT | QQRSKYPPWT |
| L31D7 | RASQSVIQSLA | RASKRAT | QQRSKWPPWT |
| AK18 | RASQSVSSYLA | DASKRAT | QQRSKWPPWT |

* = deletion

Example 2

Expression & Purification Bispecific, Bivalent <IGF-1R-EGFR> Antibody Molecules

TABLE 4

Overview of bispecific, bivalent <IGF-1R - EGFR> antibody molecules

| Construct | Sequence | scFab VH44-VL100 Disulfide |
|---|---|---|
| OA-F13B5-scFab-GA201 | SEQ ID NO: 57 (Heavy chain 1) SEQ ID NO: 58 (Heavy chain 2) SEQ ID NO: 59 (Light chain) | − |
| OA-L31D11-scFab-GA201 | SEQ ID NO: 60 (Heavy chain 1) SEQ ID NO: 61 (Heavy chain 2) SEQ ID NO: 62 (Light chain) | − |
| CM-F13B5-GA201 | SEQ ID NO: 63 (Heavy chain 1) SEQ ID NO: 64 (Heavy chain 2) SEQ ID NO: 65 | − |
| CM-L31D11-GA201 | SEQ ID NO: 66 (Light chain 1) SEQ ID NO: 67 (Light chain 2) SEQ ID NO: 68 (Heavy chain 1) SEQ ID NO: 69 (Heavy chain 2) | − |
| Tv-F13B5-GA201 | SEQ ID NO: 70 (Light chain 1) SEQ ID NO: 71 (Light chain 2) SEQ ID NO: 72 (Heavy chain) | + |
| Tv-L31D11-GA201 | SEQ ID NO: 73 (Light chain) SEQ ID NO: 74 (Heavy chain) | + |

According the procedures described in the materials and methods above, the bispecific, bivalent <IGF-1R/EGFR> antibody molecules OA-F13B5-scFab-GA201, OA-L31D11-scFab-GA201, CM-F13B5-GA201, CM-L31D11-GA201, Tv-F13B5-GA201 and Tv-L31D11-GA201 were expressed transient in HEk293 cells and purified to homogeneity.

The bispecific antibodies are based on the antigen-binding sites of a)<IGF-1R> F13B5 (SEQ ID NOs: 17-24) or <IGF-1R> L31D11 (SEQ ID NOs: 41-48) (both are affinity matured HUMAB <IGF-1R> Clone 18 antibodies) and b) humanized <EGFR>ICR62 (SEQ ID NOs: 1-8; see WO 2006/082515 abbreviated as <EGFR>ICR62). Expression of all bispecific antibodies was confirmed by Western blot. After Protein A purification of cell culture supernatants all constructs showed between 70 and 98% of bispecific antibody with the expected molecular weight as detected by analytical SEC. After SEC purification all constructs showed >97% homogenous monomer as detected by analytical SEC and a product purity between 84 and 95% in Caliper analysis.

Binding and Other Properties were Determined as Described.

The bispecific, bivalent <IGF-1R-EGFR> antibody molecules Tv-F13B5-GA201 and Tv-L31D11-GA201 (with the relevant light and heavy chain amino acid sequences given in SEQ ID NO 71-74), can be expressed and purified analogously.

Stability of Bispecific Antibodies

Denaturation Temperature (SYPRO Orange Method)

To determine the temperature at which protein denaturation (i.e. temperature-induced loss of protein structure) occurs, a method was used that relies a hydrophobic fluorescent dye (SYPRO orange, Invitrogen) that exhibits strong fluorescence in hydrophobic environments. Upon protein denaturation, hydrophobic patches become exposed to the solvent, leading to an increased fluorescence. At temperatures above the denaturation temperature, fluorescence intensities decrease again, hence the temperature at which a maximum intensity is reached is defined as the denaturation temperature. The method is described by Ericsson, U. B., et al., Anal Biochem 357 (2006) 289-298 and He, F., et al., Journal of Pharmaceutical Sciences 99 (2010) 1707-1720.

Proteins samples at a concentration of approx. 1 mg/mL in 20 mM H is/H is Cl, 140 mM NaCl, pH 6.0 were mixed with SYPRO orange (5000× stock solution) to reach a final dilution of 1:5000. A volume of 20 µL was transferred into a 384 well-plate and temperature-dependent fluorescence was recorded in a LightCycler® 480 Real-Time PCR System (Roche Applied Sciences) at a heat rate of 0.36° C./min.

Aggregation Temperature by Dynamic Light Scattering (DLS)

The temperature at which thermally induced protein aggregation occurs was determined by dynamic light scattering (DLS). DLS yields information on the size distribution of macromolecules in solution, derived from fluctuations of scattered light intensities on a microsecond scale. When samples are heated up gradually, aggregation starts at a certain temperature, giving rise to growing particle sizes. The temperature at which particle sizes begin to increase is defined as the aggregation temperature. Aggregation and denaturation temperatures need not necessarily be identical since denaturation may not necessarily be a prerequisite for aggregation.

For aggregation temperature measurements, a DynaPro DLS platereader (Wyatt technologies) was used. Preceding the measurement, samples were filtered via 384-well filter plates (Millipore MultiScreen 384-well Filtration System, 0.45 µm) into optical 384 well plates (Corning #3540). A sample volume of 35 µL was used at a protein concentration of approx. 1 mg/mL in formulation buffer (20 mM citrate, 180 mM sucrose, 20 mM arginine, 0.02% polysorbate 20). Each well was covered with 20 µL paraffin oil (Sigma) to avoid evaporation. Samples were heated from 25° C. to 80° C. at a rate of 0.05° C./min and DLS data were acquired continuously for a maximum number of 15 samples per run.

Aggregation Rate Per DLS

DLS is a sensitive method for detecting aggregates of macromolecules in solution, since aggregates give rise to strong light scattering signals. Hence, the tendency of a molecule to aggregate can be followed over time by repeated acquisition of DLS data. To accelerate potential aggregation to practical rates, measurements were conducted at 50° C.

Sample preparation was performed as described above. DLS data were recorded for up to 100 hours. Aggregation rates (nm/day) were calculated as the slope of a linear fit of average diameters over time.

Stability in Formulation Buffer

To assess bispecific molecules for their stability with regard to aggregation/fragmentation, samples were incubated for 3 weeks at 40° C. in formulation buffer (20 mM citrate, 180 mM sucrose, 20 mM arginine, 0.02% polysorbate 20) at a protein concentration of approximately 1 mg/mL. A control sample was stored for 3 weeks at −80° C.

Size exclusion chromatography for the quantification of aggregates and low-molecular weight (LMW) species was performed by HPLC. An amount of 25-100 µg of protein was applied to a Tosoh TSKgel G3000SWXL column in 300 mM NaCl, 50 mM potassium phosphate, pH 7.5 on an Ultimate3000 HPLC system (Dionex). The eluted protein was quantified by UV absorbance at 280 nm.

The IGF-1R affinity maturated bispecific <EGFR-IGF1R> antibodies OA-F13B5-scFab-GA201 and OA-L31D11-scFab-GA201 show clearly improved stability compared to unmodified OA-Ak18-scFab-GA201 (data no shown).

Example 3

Simultaneous Binding of Bispecific Antibodies to Both Antigens

The simultaneous binding of the bispecific antibody was analyzed via BIAcore as described above in Material and Methods.

Bispecific OA-F13B5-scFab-GA201 showed simultaneous binding to human EGFR and human IGF-1R. (data not shown).

Example 4

Inhibition of EGFR- as Well as IGF-1R-Signaling Pathways by Bispecific <EGFR-IGF1R> Antibodies To evaluate the potential inhibitory activity of the new affinity-maturated bispecific <EGFR-IGF1R> antibodies OA-F13B5-scFab-GA201 and OA-L31D11-scFab-GA201, the degree of inhibition of signaling towards both pathways was analyzed in tumor cells expressing different ratios of IGF-1R and EGFR and compared to the analogously constructed bispecific <EGFR-IGF1R> antibody OA-Ak18-scFab-GA201 based on the unmodified <IGF-1R> HUMAB-Clone 18 (AK18). While A549 and BxPC3 cells express both IGF-1R and EGFR, TC-71 cells express IGF-1R only.

Human tumor cells (A549, BxPC3 or TC-71, $3 \times 10^4$ cells/well) in culture medium supplemented with 10% fetal bovine serum, 2 mM L-glutamine were seeded in 96-well microtiter plates and cultivated over night at 37° C. and 5% $CO_2$. The medium was carefully removed and replaced by 100 µl serum-free culture medium (supplemented with 1 mg/ml RSA, 10 mM Hepes, 1% PenStrep) and incubated for at least 2.0 hours at 37° C. and 5% CO2. The medium was again carefully removed and replaced by 50 µl/well with a serial dilution of bispecific antibodies and control antibodies (concentration 400 nM, dilution steps 1:4) in serum-free culture medium followed by an incubation for 30 min at 37° C. and 5% $CO_2$. Cells were stimulated by the addition of 50 µl/well IGF-1 (10 nM) or EGF (20 ng/ml) (diluted in serum-free culture medium) and incubated for 10 min at 37° C. and 5% $CO_2$. The medium was carefully removed and cells were washed once with 100 µl/well of ice cold PBS. Cells are lysed by the addition of 100 µl/well BioRad Cell Lysis buffer (BioRad Cell Lysis Kit (BioRad Cat #171-304012). Plates were stored at −20° C. until further analysis. Cell debris were removed by filtering cell lysates through MultiScreen HTS-filter plates by centrifugation at 500 g for 5 min. EGFR and IGF-1R phosphorylation in filtered cell lysates were analyzed with a Luminex system using the P-EGFR (Tyr) bead kit (Millipore Cat. #46-603) for the analysis of EGFR phosphorylation and the P-IGF-1R (Tyr1131) bead kit (BioRad Cat. #171V27343) for the analysis of IGF-1R phosphorylation. The Luminex assays were performed as described in the BioPlex Phosphoprotein Detection manual (BioRad Bulletin #2903) using Phosphoprotein Detection Reagent Kits (BioRad Cat. #171-304004).

The IGF-1R affinity maturated bispecific <EGFR-IGF1R> antibodies OA-F13B5-scFab-GA201 and OA-L31D11-scFab-GA201 effectively inhibit the phosphorylation of IGF-1R and EGFR (<1 nM) (see Tables 5 and 6). The potency of IGF-1R inhibition is markedly increased when compared to unmodified OA-Ak18-scFab-GA201 (A549: 2-4×; BxPC3: 2-6×; TC-71: 25-50×).

TABLE 5

IC50 Values IGF-1R phosphorylation Assay

| Construct | Inhibition of IGF-1R phosphorylation (IC50) A549 | Inhibition of IGF-1R phosphorylation (IC50) BxPC3 | Inhibition of IGF-1R phosphorylation (IC50) TC-71 |
|---|---|---|---|
| OA-F13B5-scFab-GA201 | 0.10 nM | 0.07 nM | 0.08 nM |
| OA-L31D11-scFab-GA201 | 0.05 nM | 0.03 nM | 0.04 nM |
| OA-Ak18-scFab-GA201 | 0.21 nM | 0.18 nM | 2.00 nM |

TABLE 6

IC50 Values EGFR phosphorylation Assay

| Construct | Inhibition of EGFR phosphorylation (IC50) A549 | Inhibition of EGFR phosphorylation (IC50) BxPC3 |
|---|---|---|
| OA-F13B5-scFab-GA201 | 0.23 nM | 0.82 nM |
| OA-L31D11-scFab-GA201 | 0.19 nM | 0.47 nM |
| OA-Ak18-scFab-GA201 | 0.23 nM | 1.67 nM |

Example 5

Proliferation Inhibition of A549 and RD-ES Cancer Cells in 3D Culture by Bispecific <EGFR-IGF1R> Antibodies The bispecific <EGFR-IGF1R> antibody OA-Ak18-scFab-GA201 inhibits the growth of cancer cell lines that express IGF-1R and/or EGFR.

To evaluate the potential inhibitory activity of the affinity-maturated bispecific <EGFR-IGF1R> antibodies OA-F13B5-scFab-GA201 and OA-L31D11-scFab-GA201 in cell proliferation assays of cancer cell lines, the degree of inhibition on A549 cancer cells (which express EGFR as well as IGF-1R) and on RD-ES cancer cells (expressing IGF-1R) was analyzed.

Human tumor cells (A549 or RD-ES) were cultured in RPMI 1640 medium (PAA, Pasching, Austria) supplemented with 10% FBS (PAA), 1 mM sodium pyruvate (Gibco, Darmstadt, Germany), non-essential amino acids (Gibco) and 2 mM L-glutamine (Sigma, Steinheim, Germany). 1000 cells/well (A459 RD-ES) were seeded in 96-well poly-HEMA (poly(2-hydroxyethylmethacrylate) (Polysciences, Warrington, Pa., USA)) coated plates containing the culture medium. Concomitantly, different concentrations of bispecific antibodies or control antibodies were added and incubated for 7 days. The CellTiterGlo® (Promega, Madison, Wis., USA) assay is used to detect cell viability by measuring the ATP-content of the cells according to the manufacturer's instructions.

Figure 1B:
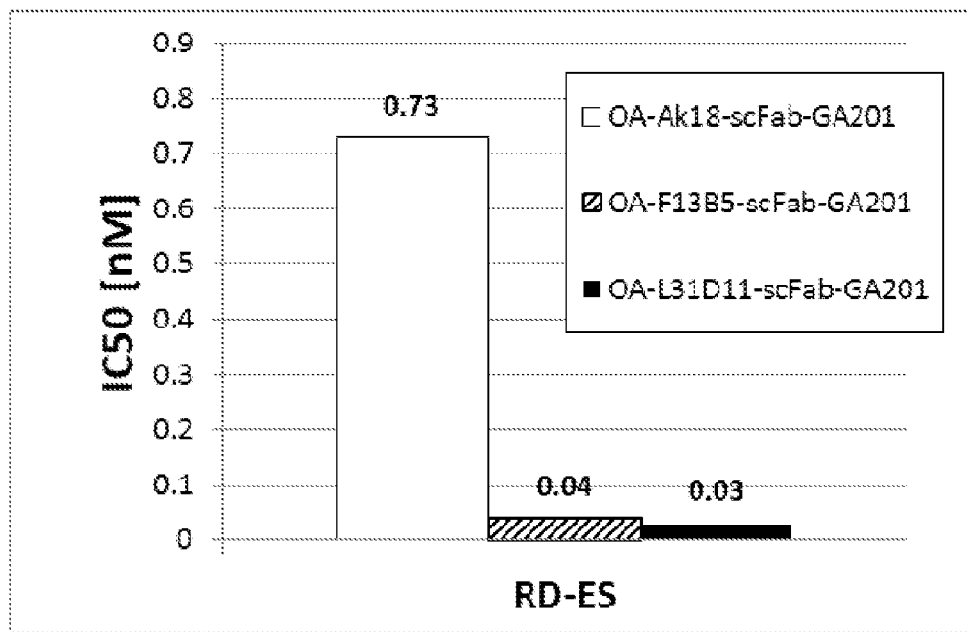

Results are shown in FIGS. 1a and 1b and Table 7. The bispecific <EGFR-IGF1R> antibodies OA-F13B5-scFab-GA201 and OA-L31D11-scFab-GA201 effectively inhibit cell proliferation of A549 and RD-ES cells (<1 nM). When compared to the non-affinity maturated unmodified bispecific <EGFR-IGF1R> antibody OA-Ak18-scFab-GA201 the potency is markedly increased for the affinity maturated bispecific antibodies according to the invention OA-F13B5-scFab-GA201 and OA-L31D11-scFab-GA201 (3-5× for A549 and ~20× for RD-ES) (see Table 7).

TABLE 7

IC 50 Values 3D Proliferation Assay

| Construct | Inhibition of cancer cell proliferation (IC50) A549 | Inhibition of cancer cell proliferation (IC50) RD-ES |
|---|---|---|
| OA-F13B5-scFab-GA201 | 0.15 nM | 0.04 nM |
| OA-L31D11-scFab-GA201 | 0.10 nM | 0.03 nM |
| OA-Ak18-scFab-GA201 | 0.50 nM | 0.73 nM |

Example 6

Binding of Bispecific <EGFR-IGF1R> Antibodies to Cells with Different EGFR And IGF-1R Expression The bispecific <EGFR-IGF1R> antibody OA-Ak18-scFab-GA201 binds to cells expressing IGF-1R and/or EGFR.

To evaluate the potential binding of the affinity-maturated bispecific <EGFR-IGF1R> antibodies OA-F13B5-scFab-GA201 and OA-L31D11-scFab-GA201 to human tumor cells, competitive binding assays were performed on cells with different IGF-1R/EGFR expression ratio.

Human tumor cells (A549 or TC-71, 2×105 cells/well) diluted in ice-cold buffer (PBS+2% FCS, Gibco) were added to a mixture of labeled monospecific IGF-1R antibody R1507 (final concentration of 1 µg/ml) and different concentrations of unlabeled IGF1R-EGFR bispecific antibodies or unlabeled monospecific antibodies or Fab fragments as controls (final titration range of 100 to 0.002 µg/ml) in a 96-well microtiter plate. The mixture was incubated on ice for 45 minutes. Cells were washed 2 times by addition of 150-200 µl buffer (PBS+2% FCS) and subsequent centrifugation (300 g; 5 min, 4° C.). The cells were then resuspended in 200 µl fixation buffer (1× CellFix, BD #340181) containing 6.25 µl/ml 7-AAD (BD #559925) and incubated for 10-20 min on ice to allow for fixation and penetration of 7-AAD in dead cells. Fluorescent signal of the samples was analyzed by FACS and IC50 values are calculated.

The results of the competitive binding analysis versus <IGF-1R> HUMAB Clone 18 (IC50 values) are shown in Table 8. On A549 tumor cells, expressing both IGF-1R and EGFR, binding of the affinity-maturated bispecific <EGFR- IGF1R> antibodies OA-F13B5-scFab-GA201 and OA-L31D11-scFab-GA201 was slightly superior to the bispecific <EGFR-IGF1R> antibody OA-Ak18-scFab (~2×). On TC-71 tumor cells, expressing IGF-1R but not EGFR, binding of the affinity-maturated bispecific <EGFR-IGF1R> antibodies OA-F13B5-scFab-GA201 and OA-L31D11-scFab-GA201 was strongly enhanced compared to the bispecific <EGFR-IGF1R> antibody OA-Ak18-scFab (10-25×). In this setting, were only IGF-1R but not EGFR is expressed 1+1 bispecific antibodies can only bind to IGF-1R with one binding arm, thus differences in IGF-1R affinity might become more crucial.

TABLE 8

IC 50 Values Cellular Binding Assay

| Construct | Binding to A549 cells (IC50) | Binding to TC-71 cells (IC50) |
|---|---|---|
| OA-F13B5-scFab-GA201 | 0.67 nM | 4.09 nM |
| OA-L31D11-scFab-GA201 | 0.39 nM | 1.59 nM |
| Unmodified OA-Ak18-scFab-GA201 | 1.06 nM | 39.94 nM |

Example 7

Preparation of the Glycoengineered Derivatives of Bispecific <EGFR-IGF1R> Antibodies Glycoengineered derivatives of bispecific <EGFR-IGF1R> antibodies were produced by co-transfecting HEK293-EBNA cells with the mammalian antibody heavy and light chain expression vectors using a calcium phosphate-transfection approach. Exponentially growing HEK293-EBNA cells were transfected by the calcium phosphate method. For the production of the glycoengineered antibody, the cells were co-transfected with a plasmid for a fusion GnTIII polypeptide expression and a second plasmid for mannosidase II expression, respectively. Plasmid ratios of bispecific antibodies were added as described in the material and methods section above. Cells were grown as adherent monolayer cultures in T flasks using DMEM culture medium supplemented with 10% FCS, and were transfected when they were between 50 and 80% confluent. For the transfection of a T75 flask, 7.5 (to 8) million cells were seeded 24 hours before transfection in ca 14 ml DMEM culture medium supplemented with FCS (at 10% V/V final), (eventually 250 µg/ml neomycin,) and cells were placed at 37° C. in an incubator with a 5% CO2 atmosphere overnight. For each T75 flask to be transfected, a solution of DNA, CaCl2 and water was prepared by mixing 47 µg total plasmid vector DNA, 235 µl of a 1M CaCl2 solution, and adding water to a final volume of 469 µl. To this solution, 469 µl of a 50 mM HEPES, 280 mM NaCl, 1.5 mM Na2HPO4 solution at pH 7.05 were added, mixed immediately for 10 sec and left to stand at room temperature for 20 sec. The suspension was diluted with ca. 12 ml of DMEM supplemented with 2% FCS, and added to the T75 in place of the existing medium. The cells were incubated at 37° C., 5% CO2 for about 17 to 20 hours, then medium was replaced with ca. 12 ml DMEM, 10% FCS. The conditioned culture medium was harvested 5 to 7 days post-transfection centrifuged for 5 min at 210-300*g, sterile filtered through a 0.22 µm filter (or alternatively centrifuged for 5 min at 1200 rpm, followed by a second centrifugation for 10 min at 4000 rpm) and kept at 4° C.

Glycoengineered antibodies were purified and formulated as described above for the non-glycoengineered antibodies. The oligosaccharides attached to the Fc region of the antibodies were analysed as described below to determine the amount of fucose.

Example 8

Binding to FcgRIIIa and ADCC In Vitro Assay of Bispecific <EGFR-IGF1R> Antibodies The degree of ADCC mediation by a given antibody depends not only on the antigen that is bound, but is also dependent on affinities of constant regions to the FcgRIIIa, which is known as the Fc receptor that triggers the ADCC reaction. For the analysis of binding of the bispecific <EGFR-IGF1R> antibodies to the FcgRIIIa, a Biacore technology was applied. By this technology, binding of bispecific <EGFR-IGF1R> antibodies to recombinantly produced FcgRIIIa domains was assessed. All surface plasmon resonance measurements were performed as described above in Material and Methods. Glycoengineered OA-F13B5-scFab-GA201-GE and OA-L31D11-scFab-GA201-GE showed a binding to human Fc Gamma RIIIa with a binding affinity of KD-value of $7.5 \times 10^{-09}$ M and $6.4 \times 10^{-09}$ M, respectively (versus $3.3 \times 10^{-08}$ M and $6.4 \times 10^{-08}$ M of the WT (nonglycoengineered versions)).

To analyze to what degree the binding competency of bispecific <EGFR-IGF1R> antibodies to FcgRIIIa translates also into in-vitro ADCC activity towards tumor cells, ADCC competency is determined in cellular assays. For these assays, glycomodified derivatives bispecific <EGFR-IGF1R> antibodies were prepared and tested in an in-vitro ADCC assay as described below.

Heparin blood was diluted 1:1 (v/v) with ice cold PBS and distributed onto the upper part of the Leucosep tubes (20-25 ml/tube). After centrifugation at 800×g at 4° C. for 30 min without brake, plasma and thrombocytes in the upper part of the supernatant were removed and the interphase containing MNC's collected in 50 ml Falcon tubes. Diluted with the same volume of ice cold PBS, tubes were centrifuged for 10 min at 450×g at 4° C. to wash out Ficoll. Pellet was resuspended in 3 ml PBS, filled up to 50 ml with PBS and spun down at 450×g at 4° C. for 10 min. This washing step was repeated once more. Pellet was resuspended in AIM-V Medium (approximately in 10 ml) and cell number was determined by counting after trypan blue staining. The cells were diluted to the adequate cell density of 500000 Z/well for a target to effector cell ratio of 1:25. The target cells were washed with PBS 2 times. The adherent cells were trypsinized to get them from the culture flask. After 5 min incubation in the incubator at 37° C. and 5% $CO_2$ the trypsin was stopped with culture medium. The cells were centrifuged with 910 rpm for 10 min. The supernatant was removed and the pellet was resuspended with culture medium and counted. 20000 target cells/well were seeded to 96well E-plate, 50 µl to each well. After the preparation of the PBMNCs the culture medium was removed from wells of E-plates. 50 µl serum free AIM-V medium, 50 µl antibody solution and 50 µl effector cells (fresh isolated PBMNCs from donors of the blood bank Roche) delivered to wells. Ratio target- to effector cells 1:25. All dilutions are made with serum free AIM-V medium. The following controls were included: target- and effector cells without antibody (=spontaneous release), target cells only, medium only and target cells with antibody without effector cells. The antibody dilutions are calculated considering the equivalent dose. This means the bispecific formats must be double concentrated and the combinations 1+1. Evaluation of ADCC was determined 3 hours and 5 hours after addition of antibodies and effector cells according following formula:

Normalization time: time of addition antibodies and effector cells

Spontaneous release: Target cells+medium w/o antibodies+effector cells

Percentage ADCC=((Normalized cell index (NCI) Spontaneous release—NCI sample)/NCI spontaneous release)×100

Figure 2A:
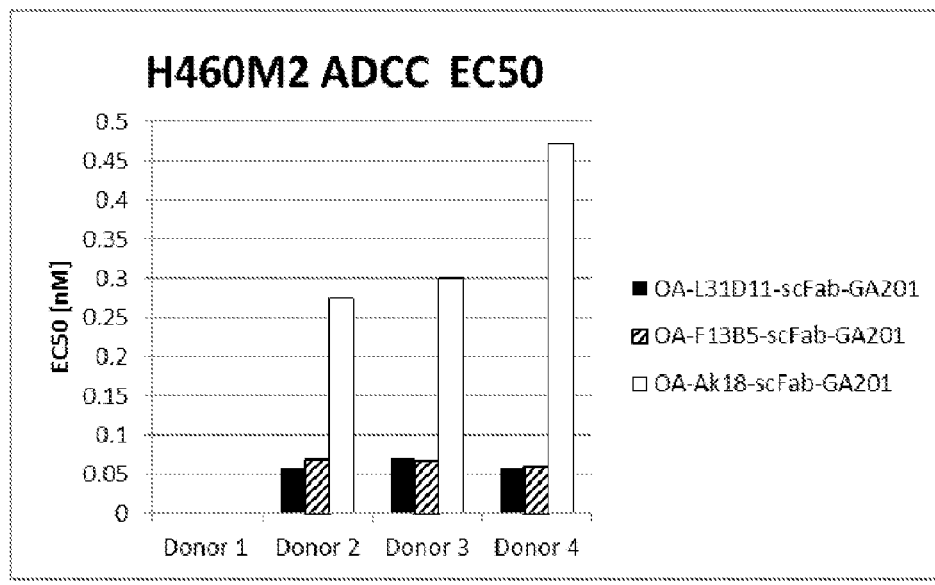
FIGS. 2a and 2b ADCC in vitro assay with two different cancer cell lines H460M2 (FIG. 2a) and H322M (FIG. 2b). Both affinity matured bispecific glycoengineered <EGFR-IGF1R> antibodies OA-F13B5-scFab-GA201-GE and OA-L31D11-scFab-GA201-GE showed a clear increase in ADCC compared to the unmodified glycoengineered bispecific <EGFR-IGF1R> antibody OA-Ak18-scFab-GA201-GE.
Figure 2B:
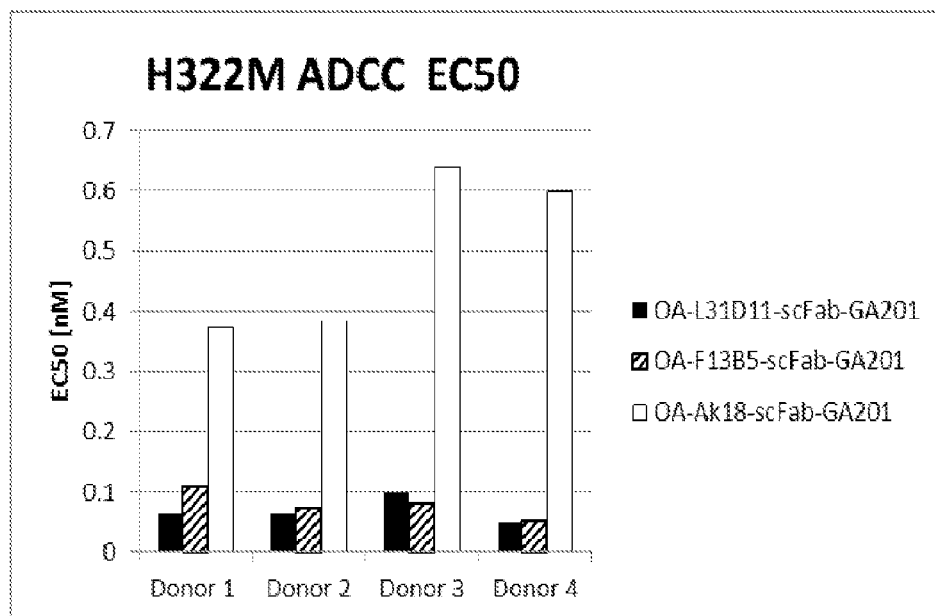

Results are shown in FIGS. 2a and 2b. Both affinity matured bispecific glycoengineered <EGFR-IGF1R> antibodies OA-F13B5-scFab-GA201-GE and OA-L31D11-scFab-GA201-GE showed a clear increase in ADCC compared to the non-affinity matured and analogously constructed bispecific glycoengineered <EGFR-IGF1R> antibody OA-Ak18-scFab-GA201-GE based on the unmodified <IGF-1R> HUMAB-Clone 18 (AK18) with two different tumor cell lines (H460M2 and H322M).

Example 9

Analysis of Glycostructure of Bispecific <EGFR-IGF1R> Antibodies

For determination of the relative ratios of fucose- and non-fucose (a-fucose) containing oligosaccharide structures, released glycans of purified antibody material was analyzed by reverse phase UPLC(RP-UPLC). For this, the glycans were released and separated from the protein using N-glycosidase F and fluorescently labeled at the reductive end with 2-AB label (2-amino benzamide). After a clean-up step to remove excess 2-AB dye, the labeled oligosaccharide pool was applied to a UPLC system equipped with a fluorescence detector. The separation of the oligosaccharide species was achieved using a reverse phase column. For the quantification of the relative levels of nonFuc content of the samples, the areas of all peaks representing oligosaccharides without fucose were summarized and related to the total peak area of all oligosaccharide peaks.

The amount of fucose was determined as follows:
OA-L31D11-scFab-GA201: 24%
OA-F13B5-scFab-GA201: 23%

The invention claimed is:

1. A bispecific antibody that binds to human EGFR and human IGF-1R comprising a first antigen-binding site that binds to human EGFR and a second antigen-binding site that binds to human IGF-1R,
   i) the first antigen-binding site comprises in the heavy chain variable domain a CDR1 of SEQ ID NO:1, a CDR2 of SEQ ID NO:2, and a CDR3 of SEQ ID NO:3, and in the light chain variable domain a CDR1 of SEQ ID NO:4, a CDR2 of SEQ ID NO:5, and a CDR3 of SEQ ID NO:6; and
   ii) the second antigen-binding site is a modified antigen-binding site based on the heavy chain variable domain comprising a CDR1 of SEQ ID NO:9, a CDR2 of SEQ ID NO:10, and a CDR3 of SEQ ID NO:11; and on the light chain variable domain comprising a CDR1 of SEQ ID NO: 12, a CDR2 of SEQ ID NO:13, and a CDR3 of SEQ ID NO:14;
   wherein the modified second antigen-binding site comprises one more modifications in one or more of the CDRs; and
   wherein the modified second antigen binding site has an at least 10-fold increased KD value of the binding affinity for binding to human IGF-1R compared to the unmodified second antigen binding site.

2. A bispecific antibody that binds to human EGFR and human IGF-1R comprising a first antigen-binding site that binds to human EGFR and a second antigen-binding site that binds to human IGF-1R, wherein
   i) the first antigen-binding site comprises in the heavy chain variable domain a CDR1 of SEQ ID NO: 1, a CDR2 of SEQ ID NO: 2, and a CDR3 of SEQ ID NO:3, and in the light chain variable domain a CDR1 of SEQ ID NO: 4, a CDR2 of SEQ ID NO:5, and a CDR3 of SEQ ID NO:6; and
   ii) a) the second antigen-binding site comprises in the heavy chain variable domain a CDR1 of SEQ ID NO:17, a CDR2 of SEQ ID NO:18, and a CDR3 of SEQ ID NO:19, and in the light chain variable domain a CDR1 of SEQ ID NO:20, a CDR2 of SEQ ID NO:21, and a CDR3 of SEQ ID NO:22; or
   b) the second antigen-binding site comprises in the heavy chain variable domain_a CDR1 of SEQ ID NO:25, a CDR2 of SEQ ID NO:26, and a CDR3 of SEQ ID NO:27, and in the light chain variable domain a CDR1 of SEQ ID NO:28, a CDR2 of SEQ ID NO:29, and a CDR3 of SEQ ID NO:30; or
   c) the second antigen-binding site comprises in the heavy chain variable domain_a CDR1 of SEQ ID NO:33, a CDR2 of SEQ ID NO:34, and a CDR3 of SEQ ID NO:35, and in the light chain variable domain a CDR1 of SEQ ID NO:36, a CDR2 of SEQ ID NO:37, and a CDR3 of SEQ ID NO:38; or
   d) the second antigen-binding site comprises in the a heavy chain variable domain a CDR1 of SEQ ID NO:41, a CDR2 of SEQ ID NO:42, and a CDR3 of SEQ ID NO:43, and in the light chain variable domain a CDR1 of SEQ ID NO:44, a CDR2 of SEQ ID NO:45, and a CDR3 of SEQ ID NO:46; or
   e) the second antigen-binding site comprises in the heavy chain variable domain a CDR1 of SEQ ID NO:49, a CDR2 of SEQ ID NO:50, and a CDR3 of SEQ ID NO:51, and in the light chain variable domain a CDR1 of SEQ ID NO:52, a CDR2 of SEQ ID NO:53, and a CDR3 of SEQ ID NO:54.

3. The bispecific antibody according to claim 2, wherein
   i) the first antigen-binding site comprises a heavy chain variable domain VH of SEQ ID NO: 7, and a light chain variable domain VL of SEQ ID NO: 8; and
   ii) a) the second antigen-binding site comprises a heavy chain variable domain VH of SEQ ID NO: 23, and a light chain variable domain VL of SEQ ID NO: 24; or b) the second antigen-binding site comprises a heavy chain variable domain VH of SEQ ID NO: 31, and a light chain variable domain VL of SEQ ID NO: 32; or
c) the second antigen-binding site comprises a heavy chain variable domain VH of SEQ ID NO: 39, and a light chain variable domain VL of SEQ ID NO: 40; or
d) the second antigen-binding site comprises a heavy chain variable domain VH of SEQ ID NO: 47, and a light chain variable domain VL of SEQ ID NO: 48; or
e) the second antigen-binding site comprises a heavy chain variable domain VH of SEQ ID NO: 55, and a light chain variable domain VL of SEQ ID NO: 56.

4. The bispecific antibody according to claim 2, wherein said antibody is bivalent, trivalent or tetravalent.

5. The bispecific antibody according to claim 2, wherein said antibody is glycosylated with a sugar chain at Asn297 whereby the amount of fucose within said sugar chain is 65% or lower.

6. A pharmaceutical formulation comprising a bispecific antibody according to claim 2.

* * * * *

```
                      SEQUENCE LISTING

<160> NUMBER OF SEQ ID NOS: 86

<210> SEQ ID NO 1
<211> LENGTH: 5
<212> TYPE: PRT
<213> ORGANISM: Artificial
<220> FEATURE:
<223> OTHER INFORMATION: heavy chain CDR1, humanized <EGFR>ICR62

<400> SEQUENCE: 1

Asp Tyr Lys Ile His
1               5

<210> SEQ ID NO 2
<211> LENGTH: 17
<212> TYPE: PRT
<213> ORGANISM: Artificial
<220> FEATURE:
<223> OTHER INFORMATION: heavy chain CDR2, humanized <EGFR>ICR62

<400> SEQUENCE: 2

Tyr Phe Asn Pro Asn Ser Gly Tyr Ser Thr Tyr Ala Gln Lys Phe Gln
1               5                   10                  15

Gly

<210> SEQ ID NO 3
<211> LENGTH: 11
<212> TYPE: PRT
<213> ORGANISM: Artificial
<220> FEATURE:
<223> OTHER INFORMATION: heavy chain CDR3, humanized <EGFR>ICR62

<400> SEQUENCE: 3

Leu Ser Pro Gly Gly Tyr Tyr Val Met Asp Ala
1               5                   10

<210> SEQ ID NO 4
<211> LENGTH: 11
<212> TYPE: PRT
<213> ORGANISM: Artificial
<220> FEATURE:
```

<223> OTHER INFORMATION: light chain CDR1, humanized <EGFR>ICR62

<400> SEQUENCE: 4

Arg Ala Ser Gln Gly Ile Asn Asn Tyr Leu Asn
1               5                   10

<210> SEQ ID NO 5
<211> LENGTH: 7
<212> TYPE: PRT
<213> ORGANISM: Artificial
<220> FEATURE:
<223> OTHER INFORMATION: light chain CDR2, humanized <EGFR>ICR62

<400> SEQUENCE: 5

Asn Thr Asn Asn Leu Gln Thr
1               5

<210> SEQ ID NO 6
<211> LENGTH: 8
<212> TYPE: PRT
<213> ORGANISM: Artificial
<220> FEATURE:
<223> OTHER INFORMATION: light chain CDR3, humanized <EGFR>ICR62

<400> SEQUENCE: 6

Leu Gln His Asn Ser Phe Pro Thr
1               5

<210> SEQ ID NO 7
<211> LENGTH: 120
<212> TYPE: PRT
<213> ORGANISM: Artificial
<220> FEATURE:
<223> OTHER INFORMATION: heavy chain variable domain, humanized
      <EGFR>ICR62-I-HHD

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser
        115                 120

<210> SEQ ID NO 8
<211> LENGTH: 108
<212> TYPE: PRT
<213> ORGANISM: Artificial
<220> FEATURE:
<223> OTHER INFORMATION: light chain variable domain, humanized
      <EGFR>ICR62 -I-KC

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr
            100                 105
```

<210> SEQ ID NO 9
<211> LENGTH: 5
<212> TYPE: PRT
<213> ORGANISM: Artificial
<220> FEATURE:
<223> OTHER INFORMATION: heavy chain CDR1, <IGF-1R> HUMAB-Clone 18

<400> SEQUENCE: 9

```
Ser Tyr Gly Met His
1               5
```

<210> SEQ ID NO 10
<211> LENGTH: 17
<212> TYPE: PRT
<213> ORGANISM: Artificial
<220> FEATURE:
<223> OTHER INFORMATION: heavy chain CDR2, <IGF-1R> HUMAB-Clone 18

<400> SEQUENCE: 10

```
Ile Ile Trp Phe Asp Gly Ser Ser Thr Tyr Tyr Ala Asp Ser Val Arg
1               5                   10                  15

Gly
```

<210> SEQ ID NO 11
<211> LENGTH: 9
<212> TYPE: PRT
<213> ORGANISM: Artificial
<220> FEATURE:
<223> OTHER INFORMATION: heavy chain CDR3, <IGF-1R> HUMAB-Clone 18

<400> SEQUENCE: 11

```
Glu Leu Gly Arg Arg Tyr Phe Asp Leu
1               5
```

<210> SEQ ID NO 12
<211> LENGTH: 11
<212> TYPE: PRT
<213> ORGANISM: Artificial
<220> FEATURE:
<223> OTHER INFORMATION: light chain CDR1, <IGF-1R> HUMAB-Clone 18

<400> SEQUENCE: 12

```
Arg Ala Ser Gln Ser Val Ser Ser Tyr Leu Ala
1               5                   10
```

<210> SEQ ID NO 13
<211> LENGTH: 7
<212> TYPE: PRT

-continued

```
<213> ORGANISM: Artificial
<220> FEATURE:
<223> OTHER INFORMATION: light chain CDR2, <IGF-1R> HUMAB-Clone 18

<400> SEQUENCE: 13

Asp Ala Ser Lys Arg Ala Thr
1               5

<210> SEQ ID NO 14
<211> LENGTH: 10
<212> TYPE: PRT
<213> ORGANISM: Artificial
<220> FEATURE:
<223> OTHER INFORMATION: light chain CDR3, <IGF-1R> HUMAB-Clone 18

<400> SEQUENCE: 14

Gln Gln Arg Ser Lys Trp Pro Pro Trp Thr
1               5                   10

<210> SEQ ID NO 15
<211> LENGTH: 118
<212> TYPE: PRT
<213> ORGANISM: Artificial
<220> FEATURE:
<223> OTHER INFORMATION: heavy chain variable domain, <IGF-1R>
      HUMAB-Clone 18

<400> SEQUENCE: 15

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 16
<211> LENGTH: 108
<212> TYPE: PRT
<213> ORGANISM: Artificial
<220> FEATURE:
<223> OTHER INFORMATION: light chain variable domain, <IGF-1R>
      HUMAB-Clone 18

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
    50                  55                  60
```

```
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Lys Trp Pro Pro
                 85                  90                  95

Trp Thr Phe Gly Gln Gly Thr Lys Val Glu Ser Lys
            100                 105

<210> SEQ ID NO 17
<211> LENGTH: 5
<212> TYPE: PRT
<213> ORGANISM: Artificial
<220> FEATURE:
<223> OTHER INFORMATION: heavy chain CDR1, <IGF-1R> F13B5
      (modified <IGF-1R> HUMAB-Clone 18)

<400> SEQUENCE: 17

Ser Tyr Gly Met His
1               5

<210> SEQ ID NO 18
<211> LENGTH: 17
<212> TYPE: PRT
<213> ORGANISM: Artificial
<220> FEATURE:
<223> OTHER INFORMATION: heavy chain CDR2, <IGF-1R> F13B5

<400> SEQUENCE: 18

Ile Ile Trp Phe Asp Gly Ser Ser Thr Tyr Tyr Ala Asp Ser Val Arg
1               5                   10                  15

Gly

<210> SEQ ID NO 19
<211> LENGTH: 9
<212> TYPE: PRT
<213> ORGANISM: Artificial
<220> FEATURE:
<223> OTHER INFORMATION: heavy chain CDR3, <IGF-1R> F13B5

<400> SEQUENCE: 19

Glu Leu Gly Arg Arg Tyr Phe Asp Leu
1               5

<210> SEQ ID NO 20
<211> LENGTH: 11
<212> TYPE: PRT
<213> ORGANISM: Artificial
<220> FEATURE:
<223> OTHER INFORMATION: light chain CDR1, <IGF-1R> F13B5

<400> SEQUENCE: 20

Arg Ala Ser Gln Ser Val Ser Ser Tyr Leu Ala
1               5                   10

<210> SEQ ID NO 21
<211> LENGTH: 7
<212> TYPE: PRT
<213> ORGANISM: Artificial
<220> FEATURE:
<223> OTHER INFORMATION: light chain CDR2, <IGF-1R> F13B5

<400> SEQUENCE: 21

Gln Ala Ser Lys Arg Ala Thr
1               5
```

```
<210> SEQ ID NO 22
<211> LENGTH: 10
<212> TYPE: PRT
<213> ORGANISM: Artificial
<220> FEATURE:
<223> OTHER INFORMATION: light chain CDR3, <IGF-1R> F13B5

<400> SEQUENCE: 22

Gln Gln Arg Ser Lys Tyr Pro Pro Trp Thr
1               5                   10

<210> SEQ ID NO 23
<211> LENGTH: 118
<212> TYPE: PRT
<213> ORGANISM: Artificial
<220> FEATURE:
<223> OTHER INFORMATION: heavy chain variable domain, <IGF-1R> F13B5

<400> SEQUENCE: 23

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 24
<211> LENGTH: 108
<212> TYPE: PRT
<213> ORGANISM: Artificial
<220> FEATURE:
<223> OTHER INFORMATION: light chain variable domain, <IGF-1R> F13B5

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gln Ala Ser Lys Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys
            100                 105

<210> SEQ ID NO 25
```

```
<211> LENGTH: 5
<212> TYPE: PRT
<213> ORGANISM: Artificial
<220> FEATURE:
<223> OTHER INFORMATION: heavy chain CDR1, <IGF-1R> L37F7
      (modified <IGF-1R> HUMAB-Clone 18)

<400> SEQUENCE: 25

Ser Tyr Gly Met His
1               5

<210> SEQ ID NO 26
<211> LENGTH: 17
<212> TYPE: PRT
<213> ORGANISM: Artificial
<220> FEATURE:
<223> OTHER INFORMATION: heavy chain CDR2, <IGF-1R> L37F7

<400> SEQUENCE: 26

Ile Ile Trp Phe Asp Gly Ser Ser Thr Tyr Tyr Ala Asp Ser Val Arg
1               5                   10                  15

Gly

<210> SEQ ID NO 27
<211> LENGTH: 9
<212> TYPE: PRT
<213> ORGANISM: Artificial
<220> FEATURE:
<223> OTHER INFORMATION: heavy chain CDR3, <IGF-1R> L37F7

<400> SEQUENCE: 27

Glu Leu Gly Arg Arg Tyr Phe Asp Leu
1               5

<210> SEQ ID NO 28
<211> LENGTH: 11
<212> TYPE: PRT
<213> ORGANISM: Artificial
<220> FEATURE:
<223> OTHER INFORMATION: light chain CDR1, <IGF-1R> L37F7

<400> SEQUENCE: 28

Arg Ala Ser Gln Ser Val Ser Ser Gln Leu Ala
1               5                   10

<210> SEQ ID NO 29
<211> LENGTH: 7
<212> TYPE: PRT
<213> ORGANISM: Artificial
<220> FEATURE:
<223> OTHER INFORMATION: light chain CDR2, <IGF-1R> L37F7

<400> SEQUENCE: 29

Lys Ala Thr Asn Arg Ala Thr
1               5

<210> SEQ ID NO 30
<211> LENGTH: 10
<212> TYPE: PRT
<213> ORGANISM: Artificial
<220> FEATURE:
<223> OTHER INFORMATION: light chain CDR3, <IGF-1R> L37F7

<400> SEQUENCE: 30

Gln Gln Arg Ser Lys Tyr Pro Pro Trp Thr
1               5                   10
```

```
<210> SEQ ID NO 31
<211> LENGTH: 118
<212> TYPE: PRT
<213> ORGANISM: Artificial
<220> FEATURE:
<223> OTHER INFORMATION: heavy chain variable domain, <IGF-1R> L37F7

<400> SEQUENCE: 31

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
            115

<210> SEQ ID NO 32
<211> LENGTH: 108
<212> TYPE: PRT
<213> ORGANISM: Artificial
<220> FEATURE:
<223> OTHER INFORMATION: light chain variable domain, <IGF-1R> L37F7

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Gln
                20                  25                  30

Leu Ala Trp Tyr Gln Gln Lys Pro Gly Gln Ala Pro Arg Leu Leu Ile
            35                  40                  45

Tyr Lys Ala Thr Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys
            100                 105

<210> SEQ ID NO 33
<211> LENGTH: 5
<212> TYPE: PRT
<213> ORGANISM: Artificial
<220> FEATURE:
<223> OTHER INFORMATION: heavy chain CDR1, <IGF-1R> L39D7
      (modified <IGF-1R> HUMAB-Clone 18)

<400> SEQUENCE: 33

Ser Tyr Gly Met His
1               5
```

<210> SEQ ID NO 34
<211> LENGTH: 17
<212> TYPE: PRT
<213> ORGANISM: Artificial
<220> FEATURE:
<223> OTHER INFORMATION: heavy chain CDR2, <IGF-1R> L39D7

<400> SEQUENCE: 34

Ile Ile Trp Phe Asp Gly Ser Ser Thr Tyr Tyr Ala Asp Ser Val Arg
1               5                   10                  15

Gly

<210> SEQ ID NO 35
<211> LENGTH: 9
<212> TYPE: PRT
<213> ORGANISM: Artificial
<220> FEATURE:
<223> OTHER INFORMATION: heavy chain CDR3, <IGF-1R> L39D7

<400> SEQUENCE: 35

Glu Leu Gly Arg Arg Tyr Phe Asp Leu
1               5

<210> SEQ ID NO 36
<211> LENGTH: 11
<212> TYPE: PRT
<213> ORGANISM: Artificial
<220> FEATURE:
<223> OTHER INFORMATION: light chain CDR1, <IGF-1R> L39D7

<400> SEQUENCE: 36

Arg Ala Ser Gln Ser Val Ser Lys Gln Leu Ala
1               5                   10

<210> SEQ ID NO 37
<211> LENGTH: 7
<212> TYPE: PRT
<213> ORGANISM: Artificial
<220> FEATURE:
<223> OTHER INFORMATION: light chain CDR2, <IGF-1R> L39D7

<400> SEQUENCE: 37

Asn Ala Ser Lys Arg Ala Thr
1               5

<210> SEQ ID NO 38
<211> LENGTH: 10
<212> TYPE: PRT
<213> ORGANISM: Artificial
<220> FEATURE:
<223> OTHER INFORMATION: light chain CDR3, <IGF-1R> L39D7

<400> SEQUENCE: 38

Gln Gln Arg Ser Lys Tyr Pro Pro Trp Thr
1               5                   10

<210> SEQ ID NO 39
<211> LENGTH: 118
<212> TYPE: PRT
<213> ORGANISM: Artificial
<220> FEATURE:
<223> OTHER INFORMATION: heavy chain variable domain, <IGF-1R> L39D7

<400> SEQUENCE: 39

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
            115

<210> SEQ ID NO 40
<211> LENGTH: 108
<212> TYPE: PRT
<213> ORGANISM: Artificial
<220> FEATURE:
<223> OTHER INFORMATION: light chain variable domain, <IGF-1R> L39D7

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Lys Gln
            20                  25                  30

Leu Ala Trp Tyr Gln Gln Lys Pro Gly Gln Ala Pro Arg Leu Leu Ile
            35                  40                  45

Tyr Asn Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys
            100                 105

<210> SEQ ID NO 41
<211> LENGTH: 5
<212> TYPE: PRT
<213> ORGANISM: Artificial
<220> FEATURE:
<223> OTHER INFORMATION: heavy chain CDR1, <IGF-1R> L31D11
      (modified <IGF-1R> HUMAB-Clone 18)

<400> SEQUENCE: 41

Ser Tyr Gly Met His
1               5

<210> SEQ ID NO 42
<211> LENGTH: 17
<212> TYPE: PRT
<213> ORGANISM: Artificial
<220> FEATURE:
<223> OTHER INFORMATION: heavy chain CDR2, <IGF-1R> L31D11

<400> SEQUENCE: 42

Ile Ile Trp Phe Asp Gly Ser Ser Thr Tyr Tyr Ala Asp Ser Val Arg
1               5                   10                  15

Gly

<210> SEQ ID NO 43
<211> LENGTH: 9
<212> TYPE: PRT
<213> ORGANISM: Artificial
<220> FEATURE:
<223> OTHER INFORMATION: heavy chain CDR3, <IGF-1R> L31D11

<400> SEQUENCE: 43

Glu Leu Gly Arg Arg Tyr Phe Asp Leu
1               5

<210> SEQ ID NO 44
<211> LENGTH: 11
<212> TYPE: PRT
<213> ORGANISM: Artificial
<220> FEATURE:
<223> OTHER INFORMATION: light chain CDR1, <IGF-1R> L31D11

<400> SEQUENCE: 44

Arg Ala Ser Arg Ser Val Tyr Ser Ser Leu Ala
1               5                   10

<210> SEQ ID NO 45
<211> LENGTH: 7
<212> TYPE: PRT
<213> ORGANISM: Artificial
<220> FEATURE:
<223> OTHER INFORMATION: light chain CDR2, <IGF-1R> L31D11

<400> SEQUENCE: 45

Lys Ala Ser Ser Arg Ala Thr
1               5

<210> SEQ ID NO 46
<211> LENGTH: 10
<212> TYPE: PRT
<213> ORGANISM: Artificial
<220> FEATURE:
<223> OTHER INFORMATION: light chain CDR3, <IGF-1R> L31D11

<400> SEQUENCE: 46

Gln Gln Arg Ser Lys Trp Pro Pro Trp Thr
1               5                   10

<210> SEQ ID NO 47
<211> LENGTH: 118
<212> TYPE: PRT
<213> ORGANISM: Artificial
<220> FEATURE:
<223> OTHER INFORMATION: heavy chain variable domain, <IGF-1R> L31D11

<400> SEQUENCE: 47

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 48
<211> LENGTH: 108
<212> TYPE: PRT
<213> ORGANISM: Artificial
<220> FEATURE:
<223> OTHER INFORMATION: light chain variable domain, <IGF-1R> L31D11

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Ser Val Tyr Ser Ser
            20                  25                  30

Leu Ala Trp Tyr Gln Gln Lys Pro Gly Gln Ala Pro Arg Leu Leu Ile
        35                  40                  45

Tyr Lys Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 49
<211> LENGTH: 5
<212> TYPE: PRT
<213> ORGANISM: Artificial
<220> FEATURE:
<223> OTHER INFORMATION: heavy chain CDR1, <IGF-1R> L31D7
      (modified <IGF-1R> HUMAB-Clone 18)

<400> SEQUENCE: 49

Ser Tyr Gly Met His
1               5

<210> SEQ ID NO 50
<211> LENGTH: 17
<212> TYPE: PRT
<213> ORGANISM: Artificial
<220> FEATURE:
<223> OTHER INFORMATION: heavy chain CDR2, <IGF-1R> L31D7

<400> SEQUENCE: 50

Ile Ile Trp Phe Asp Gly Ser Ser Thr Tyr Tyr Ala Asp Ser Val Arg
1               5                   10                  15

Gly

<210> SEQ ID NO 51
<211> LENGTH: 9
<212> TYPE: PRT
<213> ORGANISM: Artificial
<220> FEATURE:
<223> OTHER INFORMATION: heavy chain CDR3, <IGF-1R> L31D7

<400> SEQUENCE: 51
```

-continued

```
Glu Leu Gly Arg Arg Tyr Phe Asp Leu
1               5

<210> SEQ ID NO 52
<211> LENGTH: 10
<212> TYPE: PRT
<213> ORGANISM: Artificial
<220> FEATURE:
<223> OTHER INFORMATION: light chain CDR1, <IGF-1R> L31D7

<400> SEQUENCE: 52

Arg Ala Ser Gln Ser Val Ile Ser Leu Ala
1               5                   10

<210> SEQ ID NO 53
<211> LENGTH: 7
<212> TYPE: PRT
<213> ORGANISM: Artificial
<220> FEATURE:
<223> OTHER INFORMATION: light chain CDR2, <IGF-1R> L31D7

<400> SEQUENCE: 53

Arg Ala Ser Lys Arg Ala Thr
1               5

<210> SEQ ID NO 54
<211> LENGTH: 10
<212> TYPE: PRT
<213> ORGANISM: Artificial
<220> FEATURE:
<223> OTHER INFORMATION: light chain CDR3, <IGF-1R> L31D7

<400> SEQUENCE: 54

Gln Gln Arg Ser Lys Trp Pro Pro Trp Thr
1               5                   10

<210> SEQ ID NO 55
<211> LENGTH: 118
<212> TYPE: PRT
<213> ORGANISM: Artificial
<220> FEATURE:
<223> OTHER INFORMATION: heavy chain variable domain, <IGF-1R> L31D7

<400> SEQUENCE: 55

Gln Val Glu Leu Val Glu Ser Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser
        115

<210> SEQ ID NO 56
```

<211> LENGTH: 108
<212> TYPE: PRT
<213> ORGANISM: Artificial
<220> FEATURE:
<223> OTHER INFORMATION: light chain variable domain, <IGF-1R> L31D7

<400> SEQUENCE: 56

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ile Gln Ser
            20                  25                  30

Leu Ala Trp Tyr Gln Gln Lys Pro Gly Gln Ala Pro Arg Leu Leu Ile
        35                  40                  45

Tyr Arg Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys
            100                 105

<210> SEQ ID NO 57
<211> LENGTH: 450
<212> TYPE: PRT
<213> ORGANISM: Artificial
<220> FEATURE:
<223> OTHER INFORMATION: OA-F13B5-scFab-GA201 Heavy chain 1

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 58
<211> LENGTH: 695
<212> TYPE: PRT
<213> ORGANISM: Artificial
<220> FEATURE:
<223> OTHER INFORMATION: OA-F13B5-scFab-GA201 Heavy chain 2

<400> SEQUENCE: 58

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gln Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser

```
            115                 120                 125
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Gly Ser Gly Gly Gly Gly
        210                 215                 220

Ser Gly Gly Gly Ser Gly Gly Gly Ser Gly Gly Gly Ser
225                 230                 235                 240

Gly Gly Gly Ser Gly Gly Gln Val Glu Leu Val Glu Ser Gly Gly
                245                 250                 255

Gly Val Val Gln Pro Gly Arg Ser Gln Arg Leu Ser Cys Ala Ala Ser
            260                 265                 270

Gly Phe Thr Phe Ser Ser Tyr Gly Met His Trp Val Arg Gln Ala Pro
        275                 280                 285

Gly Lys Gly Leu Glu Trp Val Ala Ile Ile Trp Phe Asp Gly Ser Ser
290                 295                 300

Thr Tyr Tyr Ala Asp Ser Val Arg Gly Arg Phe Thr Ile Ser Arg Asp
305                 310                 315                 320

Asn Ser Lys Asn Thr Leu Tyr Leu Gln Met Asn Ser Leu Arg Ala Glu
                325                 330                 335

Asp Thr Ala Val Tyr Phe Cys Ala Arg Glu Leu Gly Arg Arg Tyr Phe
            340                 345                 350

Asp Leu Trp Gly Arg Gly Thr Leu Val Ser Val Ser Ser Ala Ser Thr
        355                 360                 365

Lys Gly Pro Ser Val Phe Pro Leu Ala Pro Ser Ser Lys Ser Thr Ser
370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Ser Leu Gly Thr Gln Thr Tyr Ile Cys
        435                 440                 445

Asn Val Asn His Lys Pro Ser Asn Thr Lys Val Asp Lys Lys Val Glu
450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
        515                 520                 525

Gly Val Glu Val His Asn Ala Lys Thr Lys Pro Arg Glu Glu Gln Tyr
530                 535                 540
```

```
Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
            565                 570                 575

Pro Ala Pro Ile Glu Lys Thr Ile Ser Lys Ala Lys Gly Gln Pro Arg
        580                 585                 590

Glu Pro Gln Val Cys Thr Leu Pro Pro Ser Arg Asp Glu Leu Thr Lys
    595                 600                 605

Asn Gln Val Ser Leu Ser Cys Ala Val Lys Gly Phe Tyr Pro Ser Asp
610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Val Ser
                645                 650                 655

Lys Leu Thr Val Asp Lys Ser Arg Trp Gln Gln Gly Asn Val Phe Ser
            660                 665                 670

Cys Ser Val Met His Glu Ala Leu His Asn His Tyr Thr Gln Lys Ser
        675                 680                 685

Leu Ser Leu Ser Pro Gly Lys
    690                 695
```

<210> SEQ ID NO 59
<211> LENGTH: 213
<212> TYPE: PRT
<213> ORGANISM: Artificial
<220> FEATURE:
<223> OTHER INFORMATION: OA-F13B5-scFab-GA201 Light chain

<400> SEQUENCE: 59

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 60
<211> LENGTH: 450
<212> TYPE: PRT
<213> ORGANISM: Artificial
<220> FEATURE:
<223> OTHER INFORMATION: OA- L31D11-scFab-GA201 Heavy chain 1

<400> SEQUENCE: 60

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

```
Thr Leu Pro Pro Cys Arg Asp Glu Leu Thr Lys Asn Gln Val Ser Leu
            355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 61
<211> LENGTH: 695
<212> TYPE: PRT
<213> ORGANISM: Artificial
<220> FEATURE:
<223> OTHER INFORMATION: OA- L31D11-scFab-GA201 Heavy chain 2

<400> SEQUENCE: 61

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Ser Val Tyr Ser Ser
            20                  25                  30

Leu Ala Trp Tyr Gln Gln Lys Pro Gly Gln Ala Pro Arg Leu Leu Ile
        35                  40                  45

Tyr Lys Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Gly Ser Gly Gly Gly Gly
    210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gln Val Glu Leu Val Glu Ser Gly Gly
                245                 250                 255
```

```
Gly Val Val Gln Pro Gly Arg Ser Gln Arg Leu Ser Cys Ala Ala Ser
            260                 265                 270

Gly Phe Thr Phe Ser Ser Tyr Gly Met His Trp Val Arg Gln Ala Pro
            275                 280                 285

Gly Lys Gly Leu Glu Trp Val Ala Ile Ile Trp Phe Asp Gly Ser Ser
        290                 295                 300

Thr Tyr Tyr Ala Asp Ser Val Arg Gly Arg Phe Thr Ile Ser Arg Asp
305                 310                 315                 320

Asn Ser Lys Asn Thr Leu Tyr Leu Gln Met Asn Ser Leu Arg Ala Glu
                325                 330                 335

Asp Thr Ala Val Tyr Phe Cys Ala Arg Glu Leu Gly Arg Tyr Phe
            340                 345                 350

Asp Leu Trp Gly Arg Gly Thr Leu Val Ser Val Ser Ser Ala Ser Thr
            355                 360                 365

Lys Gly Pro Ser Val Phe Pro Leu Ala Pro Ser Ser Lys Ser Thr Ser
    370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
            405                 410                 415

Thr Phe Pro Ala Val Leu Gln Ser Ser Gly Leu Tyr Ser Leu Ser Ser
            420                 425                 430

Val Val Thr Val Pro Ser Ser Ser Leu Gly Thr Gln Thr Tyr Ile Cys
            435                 440                 445

Asn Val Asn His Lys Pro Ser Asn Thr Lys Val Asp Lys Lys Val Glu
    450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
            485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
            515                 520                 525

Gly Val Glu Val His Asn Ala Lys Thr Lys Pro Arg Glu Glu Gln Tyr
    530                 535                 540

Asn Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
            565                 570                 575

Pro Ala Pro Ile Glu Lys Thr Ile Ser Lys Ala Lys Gly Gln Pro Arg
            580                 585                 590

Glu Pro Gln Val Cys Thr Leu Pro Pro Ser Arg Asp Glu Leu Thr Lys
            595                 600                 605

Asn Gln Val Ser Leu Ser Cys Ala Val Lys Gly Phe Tyr Pro Ser Asp
    610                 615                 620

Ile Ala Val Glu Trp Glu Ser Asn Gly Gln Pro Glu Asn Asn Tyr Lys
625                 630                 635                 640

Thr Thr Pro Pro Val Leu Asp Ser Asp Gly Ser Phe Phe Leu Val Ser
            645                 650                 655

Lys Leu Thr Val Asp Lys Ser Arg Trp Gln Gln Gly Asn Val Phe Ser
            660                 665                 670
```

Cys Ser Val Met His Glu Ala Leu His Asn His Tyr Thr Gln Lys Ser
            675                 680                 685

Leu Ser Leu Ser Pro Gly Lys
            690                 695

<210> SEQ ID NO 62
<211> LENGTH: 213
<212> TYPE: PRT
<213> ORGANISM: Artificial
<220> FEATURE:
<223> OTHER INFORMATION: OA- L31D11-scFab-GA201 Light chain

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 63
<211> LENGTH: 450
<212> TYPE: PRT
<213> ORGANISM: Artificial
<220> FEATURE:
<223> OTHER INFORMATION: CM-F13B5-GA201 Heavy chain 1

<400> SEQUENCE: 63

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
450

<210> SEQ ID NO 64
<211> LENGTH: 452

```
<212> TYPE: PRT
<213> ORGANISM: Artificial
<220> FEATURE:
<223> OTHER INFORMATION: CM-F13B5-GA201 Heavy chain 2

<400> SEQUENCE: 64
```

| | | | | | | | | | | | | | | |
|---|---|---|---|---|---|---|---|---|---|---|---|---|---|---|
| Gln | Val | Glu | Leu | Val | Glu | Ser | Gly | Gly | Gly | Val | Val | Gln | Pro | Gly | Arg |
| 1 | | | | 5 | | | | | 10 | | | | | 15 | |
| Ser | Gln | Arg | Leu | Ser | Cys | Ala | Ala | Ser | Gly | Phe | Thr | Phe | Ser | Ser | Tyr |
| | | | 20 | | | | | 25 | | | | | 30 | | |
| Gly | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Ile | Ile | Trp | Phe | Asp | Gly | Ser | Ser | Thr | Tyr | Tyr | Ala | Asp | Ser | Val |
| | 50 | | | | | 55 | | | | | 60 | | | | |
| Arg | Gly | Arg | Phe | Thr | Ile | Ser | Arg | Asp | Asn | Ser | Lys | Asn | Thr | Leu | Tyr |
| 65 | | | | | 70 | | | | | 75 | | | | | 80 |
| Leu | Gln | Met | Asn | Ser | Leu | Arg | Ala | Glu | Asp | Thr | Ala | Val | Tyr | Phe | Cys |
| | | | | 85 | | | | | 90 | | | | | 95 | |
| Ala | Arg | Glu | Leu | Gly | Arg | Arg | Tyr | Phe | Asp | Leu | Trp | Gly | Arg | Gly | Thr |
| | | | 100 | | | | | 105 | | | | | 110 | | |
| Leu | Val | Ser | Val | Ser | Ser | Ala | Ser | Val | Ala | Ala | Pro | Ser | Val | Phe | Ile |
| | | 115 | | | | | 120 | | | | | 125 | | | |
| Phe | Pro | Pro | Ser | Asp | Glu | Gln | Leu | Lys | Ser | Gly | Thr | Ala | Ser | Val | Val |
| | 130 | | | | | 135 | | | | | 140 | | | | |
| Cys | Leu | Leu | Asn | Asn | Phe | Tyr | Pro | Arg | Glu | Ala | Lys | Val | Gln | Trp | Lys |
| 145 | | | | | 150 | | | | | 155 | | | | | 160 |
| Val | Asp | Asn | Ala | Leu | Gln | Ser | Gly | Asn | Ser | Gln | Glu | Ser | Val | Thr | Glu |
| | | | | 165 | | | | | 170 | | | | | 175 | |
| Gln | Asp | Ser | Lys | Asp | Ser | Thr | Tyr | Ser | Leu | Ser | Ser | Thr | Leu | Thr | Leu |
| | | | 180 | | | | | 185 | | | | | 190 | | |
| Ser | Lys | Ala | Asp | Tyr | Glu | Lys | His | Lys | Val | Tyr | Ala | Cys | Glu | Val | Thr |
| | | 195 | | | | | 200 | | | | | 205 | | | |
| His | Gln | Gly | Leu | Ser | Ser | Pro | Val | Thr | Lys | Ser | Phe | Asn | Arg | Gly | Glu |
| | 210 | | | | | 215 | | | | | 220 | | | | |
| Cys | Asp | Lys | Thr | His | Thr | Cys | Pro | Pro | Cys | Pro | Ala | Pro | Glu | Leu | Leu |
| 225 | | | | | 230 | | | | | 235 | | | | | 240 |
| Gly | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Lys | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Tyr | Asn | Ser | Thr |
| | 290 | | | | | 295 | | | | | 300 | | | | |
| Tyr | Arg | Val | Val | Ser | Val | Leu | Thr | Val | Leu | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Ala | Leu | Pro | Ala | Pro |
| | | | | 325 | | | | | 330 | | | | | 335 | |
| Ile | Glu | Lys | Thr | Ile | Ser | Lys | Ala | Lys | Gly | Gln | Pro | Arg | Glu | Pro | Gln |
| | | | 340 | | | | | 345 | | | | | 350 | | |
| Val | Cys | Thr | Leu | Pro | Pro | Ser | Arg | Asp | Glu | Leu | Thr | Lys | Asn | Gln | Val |
| | | 355 | | | | | 360 | | | | | 365 | | | |
| Ser | Leu | Ser | Cys | Ala | Val | Lys | Gly | Phe | Tyr | Pro | Ser | Asp | Ile | Ala | Val |
| | 370 | | | | | 375 | | | | | 380 | | | | |

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 65
<211> LENGTH: 213
<212> TYPE: PRT
<213> ORGANISM: Artificial
<220> FEATURE:
<223> OTHER INFORMATION: CM-F13B5-GA201 Light chain 1

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 66
<211> LENGTH: 213
<212> TYPE: PRT
<213> ORGANISM: Artificial
<220> FEATURE:
<223> OTHER INFORMATION: CM-F13B5-GA201 Light chain 2

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gln Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
        195                 200                 205

Glu Pro Lys Ser Cys
    210

<210> SEQ ID NO 67
<211> LENGTH: 450
<212> TYPE: PRT
<213> ORGANISM: Artificial
<220> FEATURE:
<223> OTHER INFORMATION: CM- L31D11-GA201 Heavy chain 1

<400> SEQUENCE: 67

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Thr Asp Tyr
            20                  25                  30

Lys Ile His Trp Val Arg Gln Ala Pro Gly Gln Gly Leu Glu Trp Met
        35                  40                  45

Gly Tyr Phe Asn Pro Asn Ser Gly Tyr Ser Thr Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Cys Arg Asp Glu Leu Thr Lys Asn Gln Val Ser Leu
        355                 360                 365

Trp Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 68
<211> LENGTH: 452
<212> TYPE: PRT
<213> ORGANISM: Artificial
<220> FEATURE:
<223> OTHER INFORMATION: CM- L31D11-GA201 Heavy chain 2

<400> SEQUENCE: 68

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Thr Tyr Tyr Ala Asp Ser Val
    50                  55                  60
```

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Cys Thr Leu Pro Pro Ser Arg Asp Glu Leu Thr Lys Asn Gln Val
        355                 360                 365

Ser Leu Ser Cys Ala Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Val Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 69
<211> LENGTH: 213

```
<212> TYPE: PRT
<213> ORGANISM: Artificial
<220> FEATURE:
<223> OTHER INFORMATION: CM- L31D11-GA201 Light chain 1

<400> SEQUENCE: 69
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Asn Trp Tyr Gln Gln Lys Pro Gly Lys Ala Pro Lys Arg Leu Ile
        35                  40                  45

Tyr Asn Thr Asn Asn Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Phe Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 70
<211> LENGTH: 213
<212> TYPE: PRT
<213> ORGANISM: Artificial
<220> FEATURE:
<223> OTHER INFORMATION: CM- L31D11-GA201 Light chain 2

<400> SEQUENCE: 70
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Arg Ser Val Tyr Ser Ser
            20                  25                  30

Leu Ala Trp Tyr Gln Gln Lys Pro Gly Gln Ala Pro Arg Leu Leu Ile
        35                  40                  45

Tyr Lys Ala Ser Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Trp Pro Pro
                85                  90                  95

Trp Thr Phe Gly Gln Gly Thr Lys Val Glu Ser Lys Ser Ser Ala Ser
            100                 105                 110

```
Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
            195                 200                 205

Glu Pro Lys Ser Cys
        210

<210> SEQ ID NO 71
<211> LENGTH: 448
<212> TYPE: PRT
<213> ORGANISM: Artificial
<220> FEATURE:
<223> OTHER INFORMATION: Tv-F13B5-GA201 chain 1

<400> SEQUENCE: 71

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 72
<211> LENGTH: 466
<212> TYPE: PRT
<213> ORGANISM: Artificial
<220> FEATURE:
<223> OTHER INFORMATION: Tv-F13B5-GA201 chain 2

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gln Ala Ser Lys Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Lys Tyr Pro Pro
                85                  90                  95

Trp Thr Phe Gly Gln Gly Thr Lys Val Glu Ser Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175
```

```
Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Gly Gly Ser Gly Gly Gly Gly
210                 215                 220

Ser Gln Val Gln Leu Val Gln Ser Gly Ala Glu Val Lys Lys Pro Gly
225                 230                 235                 240

Ser Ser Val Lys Val Ser Cys Lys Ala Ser Gly Phe Thr Phe Thr Asp
                245                 250                 255

Tyr Lys Ile His Trp Val Arg Gln Ala Pro Gly Gln Cys Leu Glu Trp
            260                 265                 270

Met Gly Tyr Phe Asn Pro Asn Ser Gly Tyr Ser Thr Tyr Ala Gln Lys
        275                 280                 285

Phe Gln Gly Arg Val Thr Ile Thr Ala Asp Lys Ser Thr Ser Thr Ala
    290                 295                 300

Tyr Met Glu Leu Ser Ser Leu Arg Ser Glu Asp Thr Ala Val Tyr Tyr
305                 310                 315                 320

Cys Ala Arg Leu Ser Pro Gly Gly Tyr Tyr Val Met Asp Ala Trp Gly
                325                 330                 335

Gln Gly Thr Thr Val Thr Val Ser Ser Gly Gly Gly Ser Gly Gly
            340                 345                 350

Gly Gly Ser Gly Gly Gly Gly Ser Asp Ile Gln Met Thr Gln Ser Pro
        355                 360                 365

Ser Ser Leu Ser Ala Ser Val Gly Asp Arg Val Thr Ile Thr Cys Arg
    370                 375                 380

Ala Ser Gln Gly Ile Asn Asn Tyr Leu Asn Trp Tyr Gln Gln Lys Pro
385                 390                 395                 400

Gly Lys Ala Pro Lys Arg Leu Ile Tyr Asn Thr Asn Asn Leu Gln Thr
                405                 410                 415

Gly Val Pro Ser Arg Phe Ser Gly Ser Gly Ser Gly Thr Glu Phe Thr
            420                 425                 430

Leu Thr Ile Ser Ser Leu Gln Pro Glu Asp Phe Ala Thr Tyr Tyr Cys
        435                 440                 445

Leu Gln His Asn Ser Phe Pro Thr Phe Gly Cys Gly Thr Lys Leu Glu
    450                 455                 460

Ile Lys
465

<210> SEQ ID NO 73
<211> LENGTH: 448
<212> TYPE: PRT
<213> ORGANISM: Artificial
<220> FEATURE:
<223> OTHER INFORMATION: Tv- L31D11-GA201 chain 1

<400> SEQUENCE: 73

Gln Val Glu Leu Val Glu Ser Gly Gly Gly Val Val Gln Pro Gly Arg
1               5                   10                  15

Ser Gln Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ile Ile Trp Phe Asp Gly Ser Ser Thr Tyr Tyr Ala Asp Ser Val
    50                  55                  60
```

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
            85                  90                  95

Ala Arg Glu Leu Gly Arg Arg Tyr Phe Asp Leu Trp Gly Arg Gly Thr
            100                 105                 110

Leu Val Ser Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 74
<211> LENGTH: 466
<212> TYPE: PRT
<213> ORGANISM: Artificial
<220> FEATURE:

<223> OTHER INFORMATION: Tv- L31D11-GA201 chain 2

<400> SEQUENCE: 74

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Arg | Ser | Val | Tyr | Ser | Ser |
| | | | 20 | | | | | 25 | | | | | 30 | | |
| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 | | |
| Tyr | Lys | Ala | Ser | Ser | Arg | Ala | Thr | Gly | Ile | Pro | Ala | Arg | Phe | Ser | Gly |
| | 50 | | | | | 55 | | | | | 60 | | | | |
| Ser | Gly | Ser | Gly | Thr | Asp | Phe | Thr | Leu | Thr | Ile | Ser | Ser | Leu | Glu | Pro |
| 65 | | | | | 70 | | | | | 75 | | | | | 80 |
| Glu | Asp | Phe | Ala | Val | Tyr | Tyr | Cys | Gln | Gln | Arg | Ser | Lys | Trp | Pro | Pro |
| | | | | 85 | | | | | 90 | | | | | 95 | |
| Trp | Thr | Phe | Gly | Gln | Gly | Thr | Lys | Val | Glu | Ser | Lys | Arg | Thr | Val | Ala |
| | | | | 100 | | | | | 105 | | | | | 110 | |
| Ala | Pro | Ser | Val | Phe | Ile | Phe | Pro | Pro | Ser | Asp | Glu | Gln | Leu | Lys | Ser |
| | | | 115 | | | | | 120 | | | | | 125 | | |
| Gly | Thr | Ala | Ser | Val | Val | Cys | Leu | Leu | Asn | Asn | Phe | Tyr | Pro | Arg | Glu |
| | 130 | | | | | 135 | | | | | 140 | | | | |
| Ala | Lys | Val | Gln | Trp | Lys | Val | Asp | Asn | Ala | Leu | Gln | Ser | Gly | Asn | Ser |
| 145 | | | | | 150 | | | | | 155 | | | | | 160 |
| Gln | Glu | Ser | Val | Thr | Glu | Gln | Asp | Ser | Lys | Asp | Ser | Thr | Tyr | Ser | Leu |
| | | | | 165 | | | | | 170 | | | | | 175 | |
| Ser | Ser | Thr | Leu | Thr | Leu | Ser | Lys | Ala | Asp | Tyr | Glu | Lys | His | Lys | Val |
| | | | | 180 | | | | | 185 | | | | | 190 | |
| Tyr | Ala | Cys | Glu | Val | Thr | His | Gln | Gly | Leu | Ser | Ser | Pro | Val | Thr | Lys |
| | | | 195 | | | | | 200 | | | | | 205 | | |
| Ser | Phe | Asn | Arg | Gly | Glu | Cys | Gly | Gly | Gly | Ser | Gly | Gly | Gly | Gly |
| | 210 | | | | | 215 | | | | | 220 | | | | |
| Ser | Gln | Val | Gln | Leu | Val | Gln | Ser | Gly | Ala | Glu | Val | Lys | Lys | Pro | Gly |
| 225 | | | | | 230 | | | | | 235 | | | | | 240 |
| Ser | Ser | Val | Lys | Val | Ser | Cys | Lys | Ala | Ser | Gly | Phe | Thr | Phe | Thr | Asp |
| | | | | 245 | | | | | 250 | | | | | 255 | |
| Tyr | Lys | Ile | His | Trp | Val | Arg | Gln | Ala | Pro | Gly | Gln | Cys | Leu | Glu | Trp |
| | | | | 260 | | | | | 265 | | | | | 270 | |
| Met | Gly | Tyr | Phe | Asn | Pro | Asn | Ser | Gly | Tyr | Ser | Thr | Tyr | Ala | Gln | Lys |
| | | | 275 | | | | | 280 | | | | | 285 | | |
| Phe | Gln | Gly | Arg | Val | Thr | Ile | Thr | Ala | Asp | Lys | Ser | Thr | Ser | Thr | Ala |
| | | | 290 | | | | | 295 | | | | | 300 | | |
| Tyr | Met | Glu | Leu | Ser | Ser | Leu | Arg | Ser | Glu | Asp | Thr | Ala | Val | Tyr | Tyr |
| 305 | | | | | 310 | | | | | 315 | | | | | 320 |
| Cys | Ala | Arg | Leu | Ser | Pro | Gly | Gly | Tyr | Tyr | Val | Met | Asp | Ala | Trp | Gly |
| | | | | 325 | | | | | 330 | | | | | 335 | |
| Gln | Gly | Thr | Thr | Val | Thr | Val | Ser | Ser | Gly | Gly | Gly | Gly | Ser | Gly | Gly |
| | | | | 340 | | | | | 345 | | | | | 350 | |
| Gly | Gly | Ser | Gly | Gly | Gly | Gly | Ser | Asp | Ile | Gln | Met | Thr | Gln | Ser | Pro |
| | | | 355 | | | | | 360 | | | | | 365 | | |
| Ser | Ser | Leu | Ser | Ala | Ser | Val | Gly | Asp | Arg | Val | Thr | Ile | Thr | Cys | Arg |
| | | 370 | | | | | 375 | | | | | 380 | | | |
| Ala | Ser | Gln | Gly | Ile | Asn | Asn | Tyr | Leu | Asn | Trp | Tyr | Gln | Gln | Lys | Pro |
| 385 | | | | | 390 | | | | | 395 | | | | | 400 |

```
Gly Lys Ala Pro Lys Arg Leu Ile Tyr Asn Thr Asn Asn Leu Gln Thr
                405                 410                 415

Gly Val Pro Ser Arg Phe Ser Gly Ser Gly Ser Gly Thr Glu Phe Thr
            420                 425                 430

Leu Thr Ile Ser Ser Leu Gln Pro Glu Asp Phe Ala Thr Tyr Tyr Cys
        435                 440                 445

Leu Gln His Asn Ser Phe Pro Thr Phe Gly Cys Gly Thr Lys Leu Glu
    450                 455                 460

Ile Lys
465

<210> SEQ ID NO 75
<211> LENGTH: 1200
<212> TYPE: PRT
<213> ORGANISM: Homo sapiens

<400> SEQUENCE: 75

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300
```

```
Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
            325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720
```

```
Gly Ala Phe Gly Thr Val Tyr Lys Gly Leu Trp Ile Pro Glu Glu
            725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
        1025                1030                1035

Ser Ala Thr Ser Asn Asn Ser Thr Val Ala Cys Ile Asp Arg Asn
        1040                1045                1050

Gly Leu Gln Ser Cys Pro Ile Lys Glu Asp Ser Phe Leu Gln Arg
        1055                1060                1065

Tyr Ser Ser Asp Pro Thr Gly Ala Leu Thr Glu Asp Ser Ile Asp
        1070                1075                1080

Asp Thr Phe Leu Pro Val Pro Glu Tyr Ile Asn Gln Ser Val Pro
        1085                1090                1095

Lys Arg Pro Ala Gly Ser Val Gln Asn Pro Val Tyr His Asn Gln
        1100                1105                1110

Pro Leu Asn Pro Ala Pro Ser Arg Asp Pro His Tyr Gln Asp Pro
        1115                1120                1125

His Ser Thr Ala Val Gly Asn Pro Glu Tyr Leu Asn Thr Val Gln
```

```
            1130              1135              1140
Pro Thr Cys Val Asn Ser Thr Phe Asp Ser Pro Ala His Trp Ala
        1145              1150              1155

Gln Lys Gly Ser His Gln Ile Ser Leu Asp Asn Pro Asp Tyr Gln
        1160              1165              1170

Gln Asp Phe Phe Pro Lys Glu Ala Lys Pro Asn Gly Ile Phe Lys
        1175              1180              1185

Gly Ser Thr Ala Glu Asn Ala Glu Tyr Leu Arg Val
        1190              1195              1200

<210> SEQ ID NO 76
<211> LENGTH: 1320
<212> TYPE: PRT
<213> ORGANISM: Homo Sapiens

<400> SEQUENCE: 76

Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
                20                  25                  30

Cys Gly Pro Gly Ile Asp Ile Arg Asn Asp Tyr Gln Gln Leu Lys Arg
                35                  40                  45

Leu Glu Asn Cys Thr Val Ile Glu Gly Tyr Leu His Ile Leu Leu Ile
50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
                100                 105                 110

Tyr Asn Tyr Ala Leu Val Ile Phe Glu Met Thr Asn Leu Lys Asp Ile
                115                 120                 125

Gly Leu Tyr Asn Leu Arg Asn Ile Thr Arg Gly Ala Ile Arg Ile Glu
                130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Lys Pro Met Cys
                180                 185                 190

Glu Lys Thr Thr Ile Asn Asn Glu Tyr Asn Tyr Arg Cys Trp Thr Thr
                195                 200                 205

Asn Arg Cys Gln Lys Met Cys Pro Ser Thr Cys Gly Lys Arg Ala Cys
210                 215                 220

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
                245                 250                 255

Ala Gly Val Cys Val Pro Ala Cys Pro Pro Asn Thr Tyr Arg Phe Glu
                260                 265                 270

Gly Trp Arg Cys Val Asp Arg Asp Phe Cys Ala Asn Ile Leu Ser Ala
                275                 280                 285

Glu Ser Ser Asp Ser Glu Gly Phe Val Ile His Asp Gly Glu Cys Met
                290                 295                 300
```

-continued

```
Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
        370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Glu Gln Leu Glu Gly
                405                 410                 415

Asn Tyr Ser Phe Tyr Val Leu Asp Asn Gln Asn Leu Gln Gln Leu Trp
                420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Thr Ser Lys Asn Arg Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
        530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
        595                 600                 605

Ser Val Pro Ser Ile Pro Leu Asp Val Leu Ser Ala Ser Asn Ser Ser
    610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
        690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
```

```
              725                 730                 735
Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
            755                 760                 765

Glu Glu Leu Glu Thr Glu Tyr Pro Phe Phe Glu Ser Arg Val Asp Asn
            770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
                820                 825                 830

Asp Ile Pro Gly Pro Val Thr Trp Glu Pro Arg Pro Glu Asn Ser Ile
                835                 840                 845

Phe Leu Lys Trp Pro Glu Pro Glu Asn Pro Asn Gly Leu Ile Leu Met
                850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
                900                 905                 910

Asn Gly Ser Trp Thr Asp Pro Val Phe Phe Tyr Val Gln Ala Lys Thr
                915                 920                 925

Gly Tyr Glu Asn Phe Ile His Leu Ile Ile Ala Leu Pro Val Ala Val
                930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
                980                 985                 990

Glu Val Ala Arg Glu Lys Ile Thr  Met Ser Arg Glu Leu  Gly Gln Gly
            995                 1000                1005

Ser Phe Gly Met Val Tyr Glu  Gly Val Ala Lys Gly  Val Val Lys
        1010                1015                1020

Asp Glu Pro Glu Thr Arg Val  Ala Ile Lys Thr Val  Asn Glu Ala
        1025                1030                1035

Ala Ser Met Arg Glu Arg Ile  Glu Phe Leu Asn Glu  Ala Ser Val
        1040                1045                1050

Met Lys Glu Phe Asn Cys His  His Val Val Arg Leu  Leu Gly Val
        1055                1060                1065

Val Ser Gln Gly Gln Pro Thr  Leu Val Ile Met Glu  Leu Met Thr
        1070                1075                1080

Arg Gly Asp Leu Lys Ser Tyr  Leu Arg Ser Leu Arg  Pro Glu Met
        1085                1090                1095

Glu Asn Asn Pro Val Leu Ala  Pro Pro Ser Leu Ser  Lys Met Ile
        1100                1105                1110

Gln Met Ala Gly Glu Ile Ala  Asp Gly Met Ala Tyr  Leu Asn Ala
        1115                1120                1125

Asn Lys Phe Val His Arg Asp  Leu Ala Ala Arg Asn  Cys Met Val
        1130                1135                1140
```

```
Ala Glu Asp Phe Thr Val Lys Ile Gly Asp Phe Gly Met Thr Arg
    1145                1150                1155

Asp Ile Tyr Glu Thr Asp Tyr Tyr Arg Lys Gly Gly Lys Gly Leu
    1160                1165                1170

Leu Pro Val Arg Trp Met Ser Pro Glu Ser Leu Lys Asp Gly Val
    1175                1180                1185

Phe Thr Thr Tyr Ser Asp Val Trp Ser Phe Gly Val Val Leu Trp
    1190                1195                1200

Glu Ile Ala Thr Leu Ala Glu Gln Pro Tyr Gln Gly Leu Ser Asn
    1205                1210                1215

Glu Gln Val Leu Arg Phe Val Met Glu Gly Gly Leu Leu Asp Lys
    1220                1225                1230

Pro Asp Asn Cys Pro Asp Met Leu Phe Glu Leu Met Arg Met Cys
    1235                1240                1245

Trp Gln Tyr Asn Pro Lys Met Arg Pro Ser Phe Leu Glu Ile Ile
    1250                1255                1260

Ser Ser Ile Lys Glu Glu Met Glu Pro Gly Phe Arg Glu Val Ser
    1265                1270                1275

Phe Tyr Tyr Ser Glu Glu Asn Lys Leu Pro Glu Pro Glu Glu Leu
    1280                1285                1290

Asp Leu Glu Pro Glu Asn Met Glu Ser Val Pro Leu Asp Pro Ser
    1295                1300                1305

Ala Ser Ser Ser Ser Leu Pro Leu Pro Asp Arg His
    1310                1315                1320

<210> SEQ ID NO 77
<211> LENGTH: 107
<212> TYPE: PRT
<213> ORGANISM: Homo Sapiens

<400> SEQUENCE: 77

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 78
<211> LENGTH: 105
<212> TYPE: PRT
<213> ORGANISM: Homo Sapiens

<400> SEQUENCE: 78

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30
```

Tyr Pro Gly Ala Val Thr Val Ala Trp Lys Ala Asp Ser Ser Pro Val
            35                  40                  45

Lys Ala Gly Val Glu Thr Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 79
<211> LENGTH: 330
<212> TYPE: PRT
<213> ORGANISM: Homo Sapiens

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 80
<211> LENGTH: 330
<212> TYPE: PRT
<213> ORGANISM: Homo Sapiens

<400> SEQUENCE: 80

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 81
<211> LENGTH: 327
<212> TYPE: PRT
<213> ORGANISM: Homo Sapiens

<400> SEQUENCE: 81

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 82
<211> LENGTH: 1617
<212> TYPE: DNA
<213> ORGANISM: Artificial
<220> FEATURE:
<223> OTHER INFORMATION: Library template for Ak18 VL and VH library
      (pRJH61)

<400> SEQUENCE: 82

```
atgaaatacc tattgcctac ggcagccgct ggattgttat tactcgcggc ccagccggcc      60
atggccgaaa ttgttctgac ccagagtccg gcaaccctga gcctgagtcc gggtgaacgt     120
gcaaccctgt cttgtcgtgc aagccagagc gttagtagct acctggcctg gtatcagcag     180
aaaccgggtc aggcaccgcg tctgctgatt tatgatgcat ccaagcgtgc aaccggtatt     240
ccggcacgtt ttagcggtag cggatccggc accgatttta ccctgaccat tagcagcctg     300
gaaccggaag attttgccgt ttattattgt cagcagcgta gcaaatggcc tccgtggacc     360
tttggtcagg gcaccaaagt tgaaagcaaa cgtacggtgg ctgcaccatc tgtcttcatc     420
ttcccgccat ctgatgagca gttgaaatct ggaactgcct ctgttgtgtg cctgctgaat     480
aacttctatc ccagagaggc caaagtacag tggaaggtgg ataacgccct ccaatcgggt     540
aactcccagg agagtgtcac agagcaggac agcaaggaca gcacctacag cctcagcagc     600
accctgacgc tgagcaaagc agactacgag aaacacaaag tctacgcctg cgaagtcacc     660
catcagggcc tgagctcgcc cgtcacaaag agcttcaaca ggggagagtg tggagccgca     720
gaacaaaaac tcatctcaga agaggatctg aatggagccg cagactacaa ggacgacgac     780
gacaagggtg ccgcataata aggcgcgcca attctatttc aaggagacag tcatatgaaa     840
tacctgctgc cgaccgctgc tgctggtctg ctgctcctcg ctgcccagcc ggcgatggcc     900
caggttgaac tggttgaaag cggtggtggt gttgttcagc ctggtcgtag ccagcgtctg     960
agctgtgcag catccggatt tacctttagc agctatggca tgcactgggt tcgtcaggca    1020
ccgggtaaag gtctggaatg ggttgcaatt atttggtttg atggaagcag tacctactat    1080
gcagatagcg ttcgtggtcg ttttaccatt agccgtgata tagcaaaaa caccctgtat    1140
ctgcagatga atagcctgcg tgcagaagat accgcagttt attttgtgc acgtgaactg    1200
ggtcgtcgtt atttgatct gtggggtcgt ggcaccctgg ttagcgttag cagcgctagc    1260
accaaaggcc catcggtctt ccccctggca cctcctcca gagcacctc tgggggcaca    1320
gcggccctgg gctgcctggt caaggactac ttccccgaac cggtgacggt gtcgtggaac    1380
tcaggcgccc tgaccagcgg cgtgcacacc ttccggctg tcctacagtc ctcaggactc    1440
tactccctca gcagcgtggt gaccgtgccc tccagcagct gggcaccca gacctacatc    1500
tgcaacgtga atcacaagcc cagcaacacc aaagtggaca gaaagttga gcccaaatct    1560
tgtgacgcgg ccgcaagcac tagtgcccat caccatcacc atcacgccgc ggcatag     1617
```

<210> SEQ ID NO 83
<211> LENGTH: 83
<212> TYPE: DNA
<213> ORGANISM: Artificial
<220> FEATURE:
<223> OTHER INFORMATION: Library primer sequences AM_VL_AK18_L1_ ba

<400> SEQUENCE: 83

```
tcagcagacg cggtgcctga cccggtttct gctgataccca ggccagatag ctgctaacgc      60
tctggcttgc acgacaagac agg                                              83
```

<210> SEQ ID NO 84
<211> LENGTH: 77
<212> TYPE: DNA
<213> ORGANISM: Artificial
<220> FEATURE:
<223> OTHER INFORMATION: Library primer sequences AM_VL_AK18_L2_ fo -continued

```
<400> SEQUENCE: 84
cagaaaccgg gtcaggcacc gcgtctgctg atttatgatg cgagcaaacg tgcaaccggt      60
attccggcac gttttag                                                    77

<210> SEQ ID NO 85
<211> LENGTH: 78
<212> TYPE: DNA
<213> ORGANISM: Artificial
<220> FEATURE:
<223> OTHER INFORMATION: Library primer sequences AM_VH_AK18_H1_ ba

<400> SEQUENCE: 85
caacccattc cagacccttta cccggtgcct gacgaaccca atgcatacca taagagctaa     60
aggtaaatcc ggatgctg                                                   78

<210> SEQ ID NO 86
<211> LENGTH: 84
<212> TYPE: DNA
<213> ORGANISM: Artificial
<220> FEATURE:
<223> OTHER INFORMATION: Library primer sequences AM_VH_AK18_H2_ fo

<400> SEQUENCE: 86
aggcaccggg taaaggtctg gaatgggttg caattatttg gtttgatggc agctctacct     60
attatgcaga tagcgttcgt ggtc                                            84
```